(12) United States Patent
Taniguchi et al.

(10) Patent No.: US 12,123,848 B2
(45) Date of Patent: Oct. 22, 2024

(54) CURRENT MEASUREMENT METHOD

(71) Applicant: OSAKA UNIVERSITY, Osaka (JP)

(72) Inventors: Masateru Taniguchi, Osaka (JP);
Takahito Ohshiro, Osaka (JP);
Masakazu Sanada, Kyoto (JP);
Tadashi Miyagi, Kyoto (JP)

(73) Assignee: OSAKA UNIVERSITY, Osaka (JP)

( * ) Notice: Subject to any disclaimer, the term of this patent is extended or adjusted under 35 U.S.C. 154(b) by 530 days.

(21) Appl. No.: 17/598,726

(22) PCT Filed: Feb. 20, 2020

(86) PCT No.: PCT/JP2020/006901
§ 371 (c)(1),
(2) Date: Sep. 27, 2021

(87) PCT Pub. No.: WO2020/195413
PCT Pub. Date: Oct. 1, 2020

(65) Prior Publication Data
US 2022/0187244 A1     Jun. 16, 2022

(30) Foreign Application Priority Data

Mar. 28, 2019   (JP) .................... 2019-063813

(51) Int. Cl.
*G01N 27/49*       (2006.01)
*G01N 27/327*      (2006.01)
*G01N 33/487*      (2006.01)
(52) U.S. Cl.
CPC ....... *G01N 27/49* (2013.01); *G01N 33/48721* (2013.01)

(58) Field of Classification Search
CPC .................. G01N 27/49; G01N 33/48721
See application file for complete search history.

(56) References Cited

U.S. PATENT DOCUMENTS

2006/0207880 A1   9/2006   Joyce et al.
2010/0084276 A1*  4/2010   Lindsay ............ G01N 27/3276
                                              204/403.01

(Continued)

FOREIGN PATENT DOCUMENTS

EP      1702684 A2 *  9/2006  ............... B01L 3/00
JP      2006-258813 A  9/2006
WO      2011/108540 A1  9/2011

OTHER PUBLICATIONS

Heerema et al., "Probing DNA Translocations with Inplane Current Signals in a Graphene Nanoribbon with a Nanopore," ACS Nano, Dec. 2018, 2623-2633 with Supporting Information (Year: 2018).*

(Continued)

*Primary Examiner* — Alexander S Noguerola
(74) *Attorney, Agent, or Firm* — Rimon P.C.

(57) ABSTRACT

A current measurement method for measuring a tunneling current in biopolymers passing through between a pair of electrodes includes arranging the electrodes in a liquid that contains an electrolyte and, while applying a voltage between the electrodes, measuring a current flowing between the electrodes via an electric double layer formed along surfaces of the electrodes. This enables measuring the current in consideration of the electric double layer. As a result, it is possible to more accurately measure the tunneling current in the biopolymers included in a liquid sample that contains an electrolyte.

10 Claims, 23 Drawing Sheets

(56) References Cited

U.S. PATENT DOCUMENTS

2014/0300339 A1    10/2014   Taniguchi et al.
2018/0223354 A1     8/2018   Chang et al.

OTHER PUBLICATIONS

Morrow et al., "The time-dependent development of electric double-layers in pure water at metal electrodes: the effect of an applied voltage on the local pH," Proceedings of the Royal Society A, Aug. 10, 2011, vol. 468/Iss.2137, pp. 18-34.
Takahito Ohshiro, "Development of Single-molecule Electrical Analysis for a High-throughput Single-molecule Sequencer," Bunseki Kagaku, 2017, vol. 66/No. 5, pp. 351-362, with English Abstract.
International Search report issued in corresponding International Patent Application No. PCT/JP2020/006901, dated Apr. 7, 2020, with English translation.

* cited by examiner

CURRENT MEASUREMENT METHOD

CROSS REFERENCE TO RELATED APPLICATIONS

This application is the U.S. National Phase under 35 U.S.C. § 371 of International Application No. PCT/JP2020/006901, filed on Feb. 20, 2020, which claims the benefit of Japanese Application No. 2019-063813, filed on Mar. 28, 2019, the entire contents of each are hereby incorporated by reference.

TECHNICAL FIELD

The present invention relates to a current measurement method for measuring a tunneling current in biopolymers passing through between a pair of electrodes.

BACKGROUND ART

Methods are conventionally known in which specific molecules or atoms are measured or identified using electrodes having fine tip portions. For example, Patent Document 1 discloses a method for identifying specific molecules, using fine electrodes. The unimolecular identification method described in Patent Literature 1 uses a pair of electrodes having a short interelectrode distance to measure a tunneling current in single molecules that form biopolymers passing through between the electrodes and to identify the single molecules.

PRIOR ART DOCUMENT

Patent Document

Patent Document 1: International Publication No. 2011/108540

SUMMARY OF INVENTION

Problems to be Solved by Invention

In order to measure a tunneling current between electrodes for the purpose of identifying biopolymers as described in Patent Literature 1, it is necessary to accurately adjust the distance between the electrodes. At this time, a pair of electrodes is arranged in a liquid sample containing biopolymers.

In the case where a liquid for floating biopolymers contains an electrolyte and when a voltage is applied between the electrodes, the behavior of the current flowing between the electrodes is affected by an electric double layer that is formed in the vicinity of the surfaces of the electrodes due to, for example, ion migration or the arrangement of dipoles of the solvent and the solute in the liquid. However, Patent Literature 1 fails to consider such an influence that ions or molecules such as dipoles contained in the liquid used in the liquid sample have on the current. Thus, use of an electrolyte-containing liquid in a liquid sample may become a cause of misoperation or analysis errors during operation made to the electrodes or during analysis of current values.

The present invention has been made in light of such circumstances, and it is an object of the present invention to provide a current measurement method for more accurately measuring a tunneling current in biopolymers included in a liquid sample that contains an electrolyte.

Means for Solving Problems

To solve the above-described problem, a first aspect of the present application is a current measurement method for measuring a tunneling current in a biopolymer passing through between a pair of electrodes. The current measurement method includes a) arranging the pair of electrodes in a liquid that contains an electrolyte and, while applying a voltage between the pair of electrodes, measuring a current flowing between the pair of electrodes via an electric double layer formed along surfaces of the pair of electrodes.

A second aspect of the present application is the current measurement method of the first aspect that further includes b) with the pair of electrodes having a fixed interelectrode distance, measuring the current flowing between the pair of electrodes while applying a predetermined voltage, starting from a condition in which no voltage is applied between the pair of electrodes, and c) calculating a feature quantity resulting from the electric double layer for a value of the current measured in the operation b).

A third aspect of the present application is the current measurement method of the second aspect, in which the operation b) and the operation c) are performed before the operation a), and the operation a) has measurement timing determined based on the feature quantity.

A fourth aspect of the present application is the current measurement method of the second aspect, in which the feature quantity is a time constant of the value of the current measured in the operation b).

A fifth aspect of the present application is the current measurement method of the fourth aspect, in which a plurality of said time constants are calculated in said operation c).

A sixth aspect of the present application is the current measurement method of the fourth or fifth aspect, in which the operation b) and the operation c) are performed before the operation a), and the operation a) has measurement timing determined based on the time constant.

A seventh aspect of the present application is the current measurement method of the fifth aspect, in which the operation a) is a calibration-current measurement operation of acquiring a value of the current flowing between the pair of electrodes through an operation of changing an interelectrode distance of the pair of electrodes while applying a predetermined voltage between the pair of electrodes. The operation a) includes p1) standing by for a standby time calculated based on the time constant, p2) acquiring a value of a manipulated variable that is used to change the interelectrode distance and the value of the current flowing between the pair of electrodes, and p3) changing the manipulated variable to change the interelectrode distance.

An eighth aspect of the present application is the current measurement method of the seventh aspect that further includes d) calculating an approximation function by approximation of functions of relationships between a plurality of said manipulated variables and a plurality of said current values in the operation a).

A ninth aspect of the present application is the current measurement method of the seventh aspect, in which the standby time in the operation p1) is calculated as a constant multiple of the time constant.

A tenth aspect of the present application is the current measurement method of the fifth aspect that further includes e) measuring a value of a reference current flowing between the pair of electrodes that has an interelectrode distance at which a tunneling current does not flow between the pair of electrodes, and f) calculating a target total current value by adding the value of the reference current measured in the operation e) and a value of a tunneling current corresponding to a target interelectrode distance. The operation e) and the operation f) are performed after the operation b) and the operation c), and are performed before the operation a). The operation a) includes q1) standing by for a standby time calculated based on the time constant, q2) measuring a base current flowing between the pair of electrodes, and q3) manipulating the interelectrode distance in a direction of making a value of the base current closer to the target total current value calculated in the operation f). The operation q1), the operation q2), and the operation q3) are repeatedly performed a plurality of times.

An eleventh aspect of the present application is the current measurement method of the fifth aspect that further includes g) measuring a value of a reference current flowing between the pair of electrodes that has an interelectrode distance at which a tunneling current does not flow between the pair of electrodes, and h) calculating an intermediate target total current value by adding the value of the reference current measured in the operation g) and a value of a tunneling current corresponding to an intermediate target interelectrode distance. The operation g) and the operation h) are performed after the operation b) and the operation c), and are performed before the operation a). The operation a) includes r1) standing by for a standby time calculated based on the time constant, r2) measuring a base current flowing between the pair of electrodes, and r3) manipulating the interelectrode distance in a direction of making a value of the base current closer to the intermediate target total current value calculated in the operation h). The operation r1), the operation r2), and the operation r3) are repeatedly performed a plurality of times. The current measurement method further includes i) adjusting the interelectrode distance by manipulating a manipulated variable calculated in advance from an intermediate target interelectrode distance to a final target interelectrode distance to make the interelectrode distance match with the final target interelectrode distance. The operation i) is performed after the operation a).

Effects of Invention

According to the first to eleventh aspects of the present application, it is possible to measure the current in consideration of the electric double layer.

In particular, according to the second to eleventh aspects of the present application, it is possible to reduce the occurrence of errors resulting from a transient phenomenon that may be caused by the electric double layer or other factors.

DESCRIPTION OF EMBODIMENTS

An embodiment of the present invention will be described hereinafter with reference to the accompanying drawings. In the description of the present application, the direction along the thickness of an electrode substrate is the up-down direction, a metal layer side of a substrate layer is the upper side, and a substrate layer side of a metal layer is the lower side. It is, however, noted that the electrode substrate during use does not necessarily have to be oriented with the metal layer side facing vertically upward.

1. Configurations of Electrode Substrate and Current Measurement Apparatus

Figure 1:
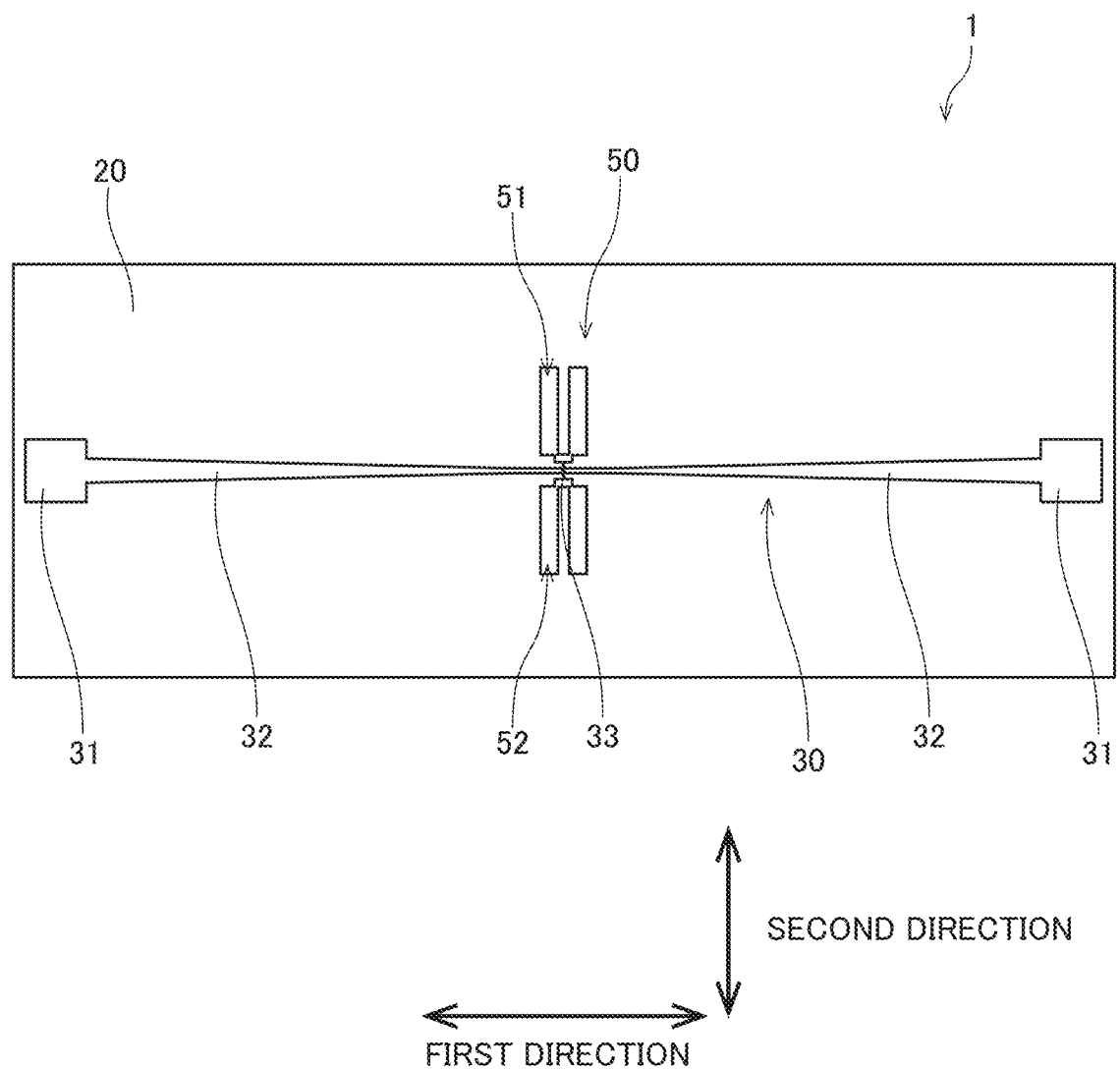
FIG. 1 is a top view of an electrode substrate.
Figure 2:
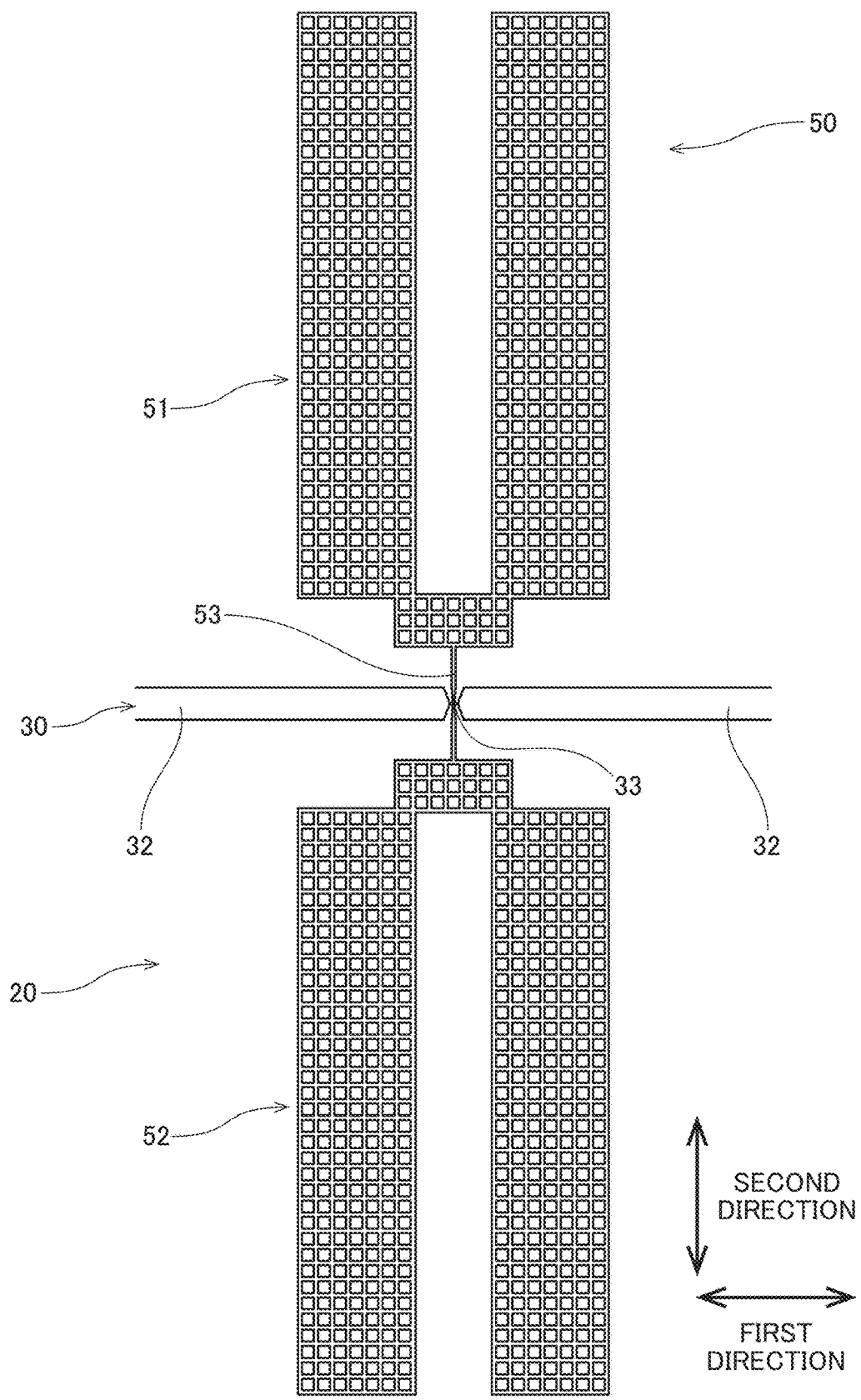
FIG. 2 is a partial top view of the electrode substrate.
Figure 3:
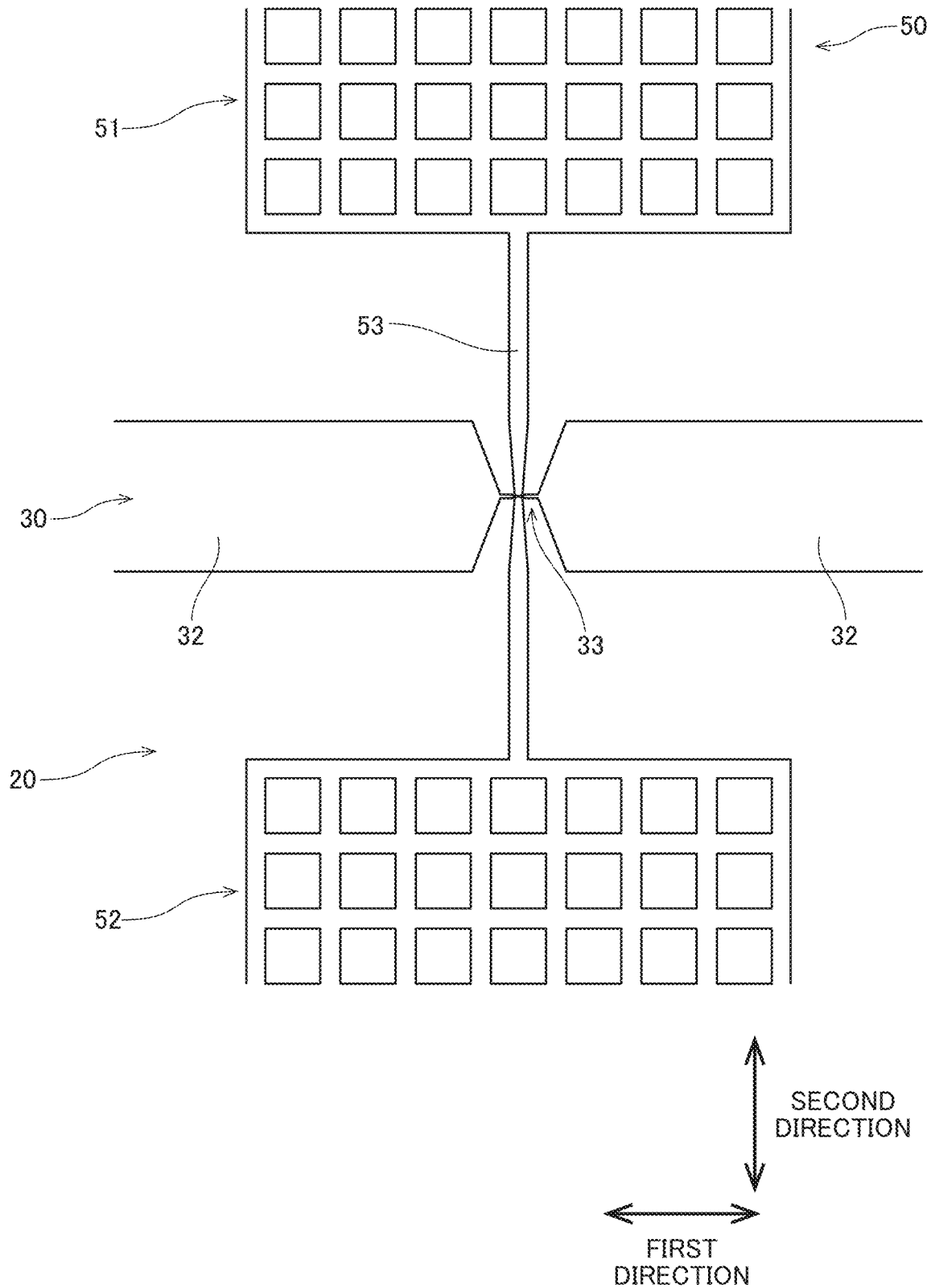
FIG. 3 is a partial top view of the electrode substrate.
Figure 4:
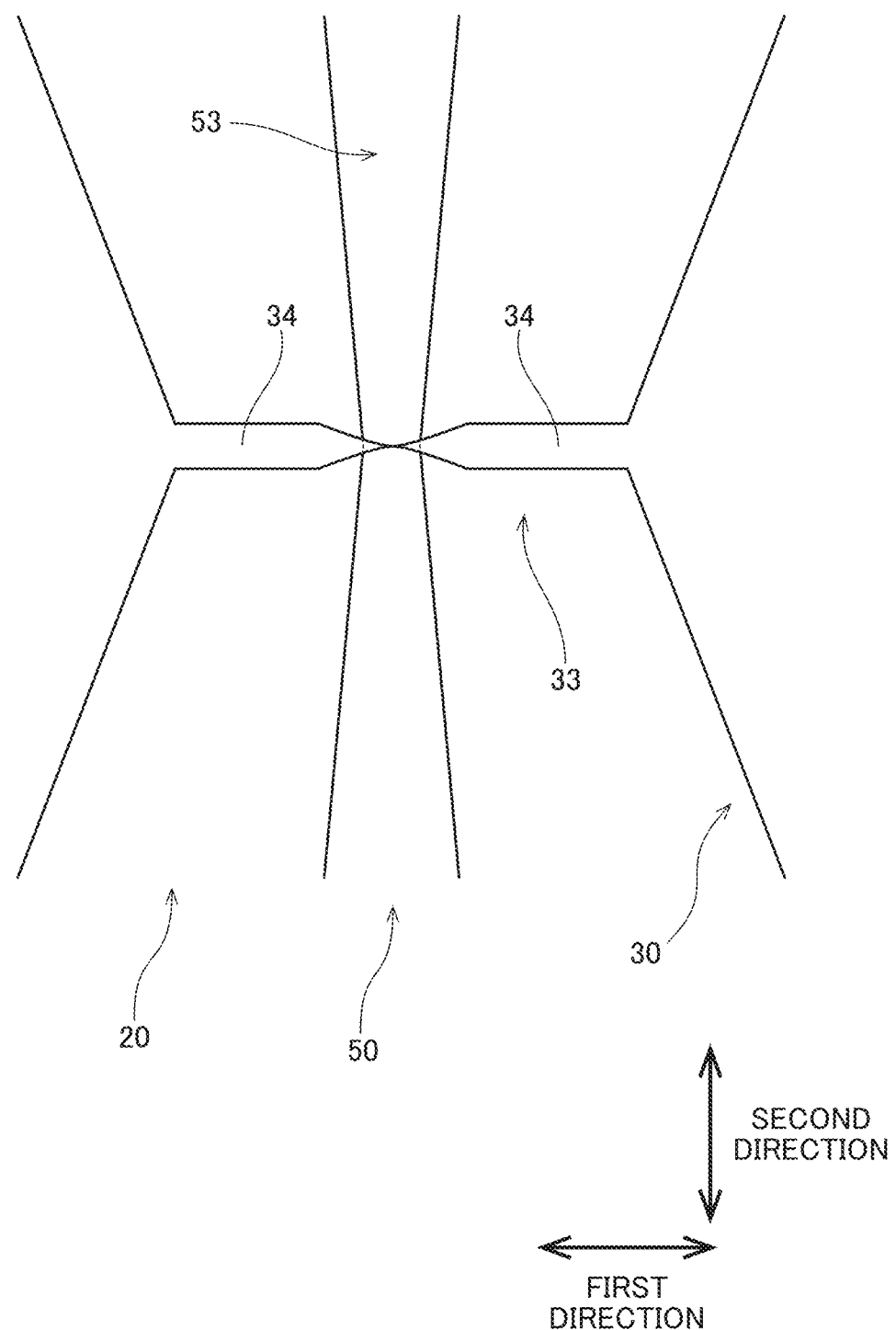
FIG. 4 is a partial top view of the electrode substrate.
Figure 5:
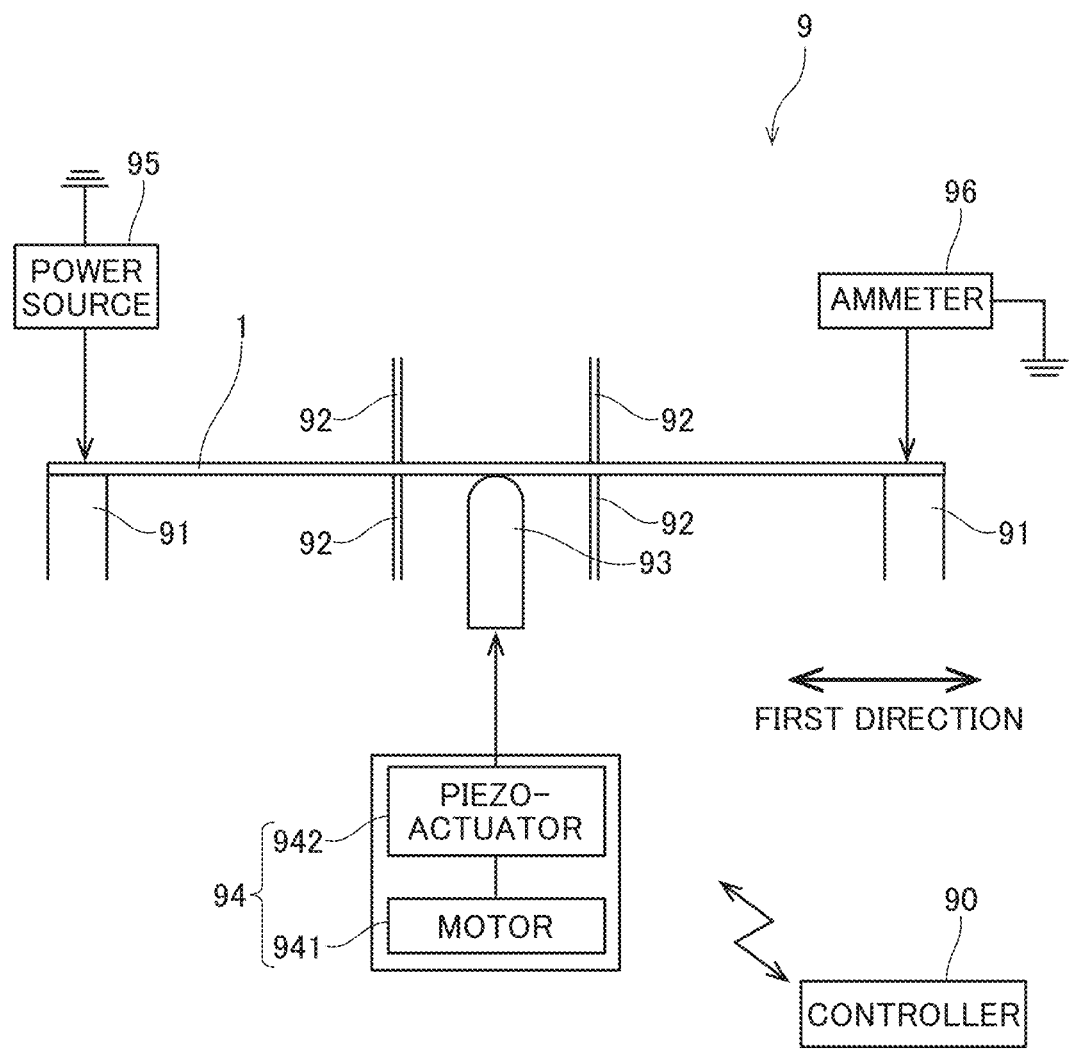
FIG. 5 is a schematic diagram illustrating how the electrode substrate is pushed and bent.
Figure 6:
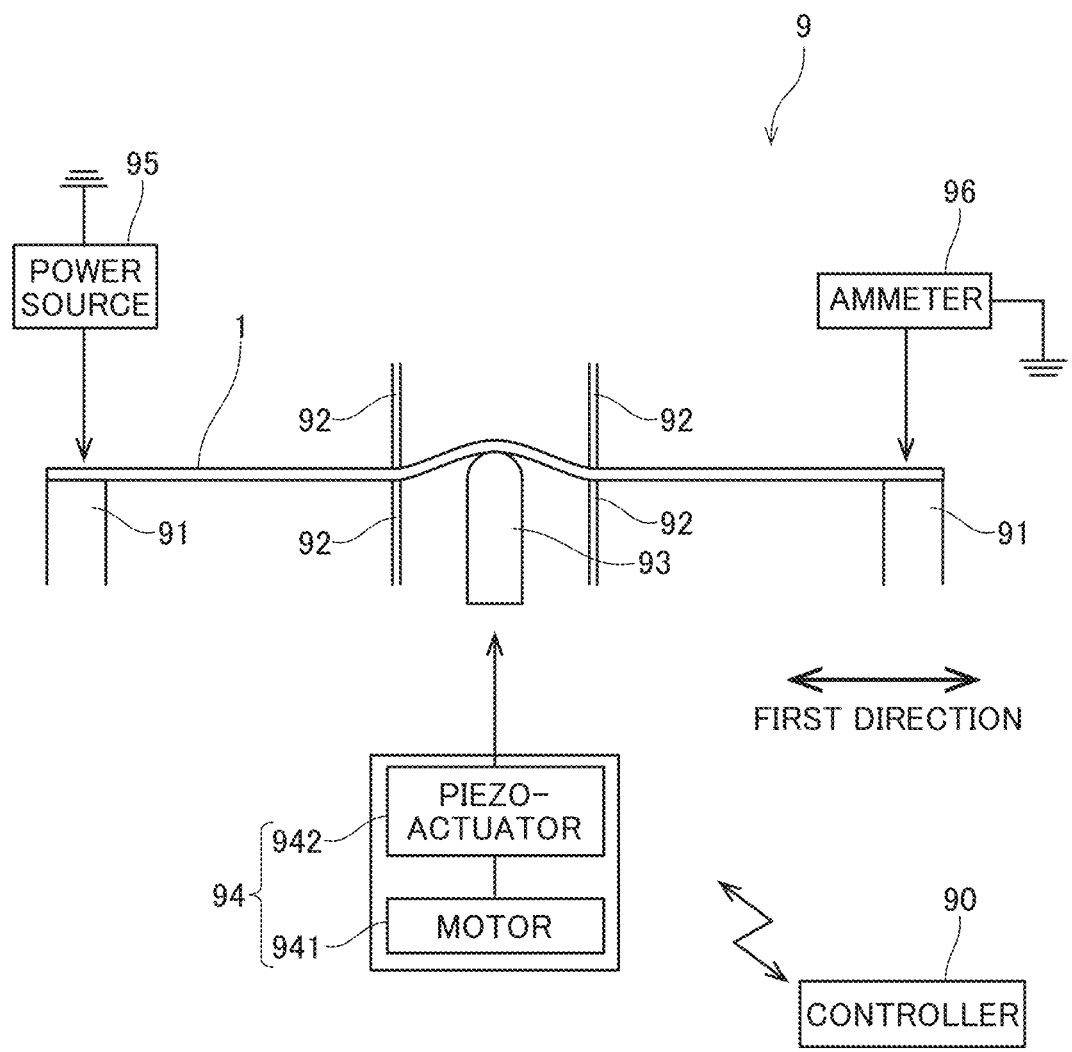
FIG. 6 is a schematic diagram illustrating how the electrode substrate is pushed and bent.
Figure 7:
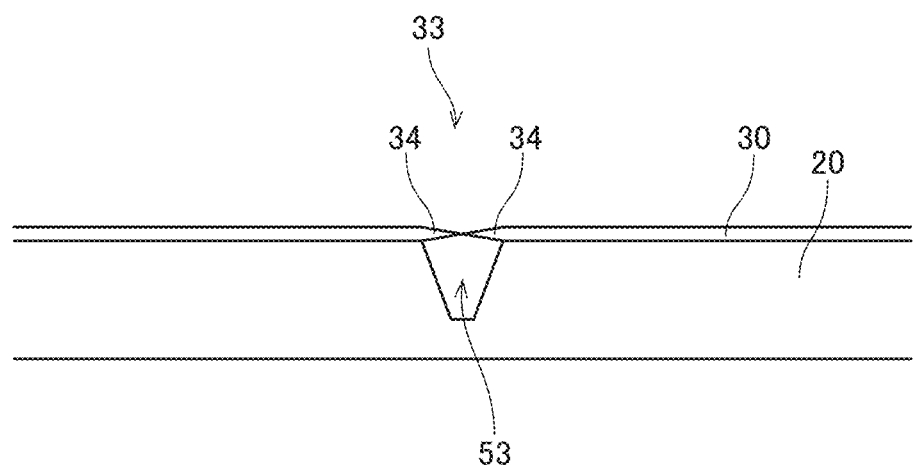
FIG. 7 is a schematic partial sectional view illustrating how the electrode substrate is pushed and bent.
Figure 8:
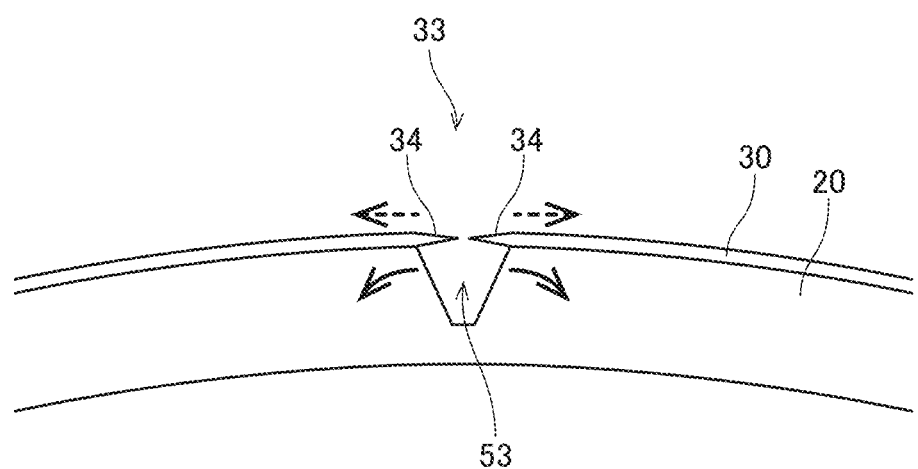
FIG. 8 is a schematic partial sectional view illustrating how the electrode substrate is pushed and bent.

An electrode substrate 1 and a current measurement apparatus 9 according to one embodiment of the present invention will be described with reference to FIGS. 1 to 8. FIG. 1 is a top view of the electrode substrate 1. FIGS. 2 to 4 are partial top views of the electrode substrate 1. FIGS. 5 and 6 are schematic diagrams illustrating how the electrode substrate 1 is pushed and bent in the current measurement apparatus 9. FIGS. 7 and 8 are schematic partial sectional views illustrating how the electrode substrate 1 is pushed and bent.

The electrode substrate 1 and the current measurement apparatus 9 are used to analyze single molecules such as amino acids that form proteins as biopolymers, nucleotides that form nucleic acids (DNA, RNA) as biopolymers, monosaccharides that form sugar chains as biopolymers, and single molecules that form other biopolymers, and to analyze sequences of such single molecules. Specifically, biopolymers are passed through between nano-electrodes 34, which will be described later, while voltage applied between the nano-electrodes 34. The current measurement apparatus 9 then detect a tunneling current flowing between the nano-electrodes 34 and the biopolymers during that period of time, and analyze the tunneling current to analyze single molecules forming the biopolymers.

As illustrated in FIG. 1, the electrode substrate 1 is a generally rectangular plate-like substrate. As illustrated in FIGS. 1 to 4, 7, and 8, the electrode substrate 1 includes a substrate layer 20 and a metal layer 30. In the following description, the longitudinal direction of the electrode substrate 1 is referred to as a first direction, and the short direction of the electrode substrate 1 is referred to as a second direction. The second direction is orthogonal to the first direction. The term "orthogonal to" as used herein also includes a meaning of "approximately orthogonal to."

The substrate layer 20 according to the present embodiment is made of an insulating material. The substrate layer 20 according to the present embodiment has a two-layer layer structure in which a substrate layer made of polyimide is overlaid on a substrate layer made of silicon (Si). In the present embodiment, the substrate layer 20 has the two-layer structure, but the present invention is not limited to this example, and the substrate layer 20 may be composed of only a single layer made of a single type of material or may be composed of three or more layers. As another alternative, the substrate layer 20 may be made of a material other than silicon and polyimide, such as polyethylene terephthalate resin, ceramic, silicone rubber, or alumina, as long as the material has insulating properties.

As illustrated in FIGS. 1 to 4, the metal layer 30 includes two connection electrode portions 31, interconnection portions 32 extending in the first direction between the two connection electrode portions 31, and a measurement electrode portion 33 arranged in the center of the interconnection portions 32.

The metal layer 30 is made of, for example, a metal serving as a conductor, such as gold (Au), platinum (Pt), silver (Ag), copper (Cu), or tungsten (W). The metal layer 30 may be composed by overlaying a plurality of metal layers. One exemplary structure may be such that a metal layer made of a metal such as gold, platinum, silver, or copper as described above is overlaid on a metal layer made of chromium (Cr). Even in that case, the measurement electrode portion 33 is preferably composed of only a single metal layer. The metal layer 30 may have a thickness of, for example, 50 to 300 nm.

The uppermost surface of substrate layer 20 and the metal layer 30 is covered with an insulation film (not shown). When the measurement electrode portion 33 is used in a liquid, it is possible, by covering the surface of the metal layer 30 with an insulation film, to reduce the occurrence of electron exchange between the liquid and the metal of the metal layer 30 in portions of the metal layer 30 other than the measurement electrode portion 33. In the present embodiment, the insulation film is a TEOS oxide film, but the insulation film may be made of any other material as long as the material has insulating properties. Note that the insulation film is not formed on at least part of the upper surface of the connection electrode portion 31. Thus, at least part of the upper surface of the connection electrode portion 31 is exposed.

The two connection electrode portions 31 are arranged apart from each other in the first direction. The two interconnection portions 32 each have a width gradually decreasing from the connection electrode portions 31 toward the measurement electrode portion 33. The measurement electrode portion 33 that has a smaller width in the second direction than the interconnection portion 32 is arranged between the interconnection portions 32 on both sides. As illustrated in FIG. 4, the measurement electrode portion 33 includes a pair of nano-electrodes 34. When no load (external force) is applied to the electrode substrate 1, the pair of nano-electrodes 34 is located such that their tip portions are in contact with each other as illustrated in FIG. 4.

The substrate layer 20 has a flow path 50 that is recessed downward from the upper surface as illustrated in FIGS. 1 to 4. The flow path 50 includes a first flow path 51, a second flow path 52, and a measurement flow path 53. The first flow path 51 and the second flow path 52 are arranged facing each other in the second direction, with the measurement electrode portion 33 sandwiched therebetween. The measurement flow path 53 is a groove extending in the second direction. The measurement flow path 53 connects the first flow path 51 and the second flow path 52 in the second direction.

The first flow path 51 and the second flow path 52 each include a plurality of grooves connected to one another in grid form. When the first flow path 51 and the second flow path 52 are filled with a liquid that contains biopolymers, each biopolymer can be readily arranged in the direction of extension of the grooves by such a shape. This reduces the possibility that boundary portions between the measurement flow path 53 and the first and second flow paths 51 and 52 may be clogged with the biopolymers. Accordingly, it is possible to suppress a reduction in flowability of the liquid in the boundary portions and to arrange each biopolymer in the direction of extension of the measurement flow path 53 in the measurement flow path 53. The grooves of the first flow path 51 and the second flow path 52 each have a width of approximately 1 μm and a depth of approximately 2 μm.

The measurement flow path 53 extends in the second direction. The measurement flow path 53 is arranged in a position where the measurement flow path 53 overlaps with the tip portions of the nano-electrodes 34 in the up-down direction. This makes it easy for biomolecules that migrate in the second direction in the measurement flow path 53 to readily pass through between the nano-electrodes 34.

Like the first flow path 51 and the second flow path 52, the measurement flow path 53 has a depth of approximately 2 μm. The measurement flow path 53 has a width that is narrow in the vicinity of the nano-electrodes 34. This allows the biopolymers to readily pass through between the nano-electrodes 34, with their orientations aligned along the second direction, i.e., the direction of extension of the measurement flow path 53, during measurement of the current value.

Next, the current measurement apparatus 9 will be described with reference to FIGS. 5 and 6. FIGS. 5 and 6 are diagrams illustrating how the current measurement apparatus 9 makes current measurements. FIG. 5 is a side view illustrating an initial state of the current measurement apparatus 9 with the electrode substrate 1 set therein. FIG. 6 is a side view illustrating the current measurement apparatus 9 when the electrode substrate 1 is pushed and bent. In FIG. 6, deformation of the electrode substrate 1 is illustrated in an exaggerated manner.

As schematically illustrated in FIG. 6, the current measurement apparatus 9 includes a placement base 91, fixtures 92, a pushing-up device 93, an elevating mechanism 94, a power source 95, an ammeter 96, and a controller 90.

The placement base 91 has a flat upper surface on which the electrode substrate 1 is arranged. The fixtures 92 according to the present embodiment correspond to four plate-like members arranged approximately perpendicular to the first direction. The fixtures 92 press and fix the electrode substrate 1 from above and below at two positions in the first direction where the measurement electrode portion 33 is placed therebetween.

The pushing-up device 93 is a circular columnar member with a hemispherical upper face. The pushing-up device 93 is connected to the elevating mechanism 94. The elevating mechanism 94 includes a motor 941 and a piezo-actuator 942. The motor 941 moves the pushing-up device 93 up and down by a great amount in units of millimeters. The piezo-actuator 942 moves the pushing-up device 93 up and down by a small amount in units of nanometers. The elevating mechanism 94 accomplishes both great and small movements by combination of the motor 941 and the piezo-actuator 942. Note that the elevating mechanism 94 may be a mechanism using other power as long as the mechanism is capable of controlling a height of pushup.

The power source 95 applies a voltage between the pair of connection electrode portions 31. The ammeter 96 measures a current value of the current flowing between the nano-electrodes 34 of the measurement electrode portion 33.

The controller 90 electrically connects and controls the elevating mechanism 94, the power source 95, and the ammeter 96. The controller 90 according to the present embodiment is configured as a computer that includes a processing unit such as a CPU, a memory such as a RAM, and a storage such as a hard disk drive. Functions of the controller 90 are implemented by the processing unit operating in accordance with computer programs stored in the storage.

In the case of setting the electrode substrate 1 in the current measurement apparatus 9, first, the electrode substrate 1 is placed on the placement base 91. Thereafter, the electrode substrate 1 is fixed from above and below with the four fixtures 92, with no load applied to the vicinity of the measurement electrode portion 33 of the electrode substrate 1. At this time, the electrode substrate 1 is arranged such that the pushing-up device 93 is located immediately under the measurement electrode portion 33.

Then, in the case of measuring current, first, the power source 95 applies a predetermined voltage between the connection electrode portions 31, and the ammeter 96 starts to measure a current value. Then, the elevating mechanism 94 is driven to push the pushing-up device 93 upward so as to adjust the distance between the tip portions of the nano-electrodes 34 (interelectrode distance).

FIG. 7 is a partial sectional view of the electrode substrate 1 in an initial position. FIG. 8 is a partial sectional view of the electrode substrate 1 that has been pushed up. When the electrode substrate 1 is not pushed and bent, the tip portions of the nano-electrodes 34 are in contact with each other as illustrated in FIGS. 4 and 7. When the pushing-up device 93 is pushed up as illustrated in FIG. 8, a portion of the electrode substrate 1 around the measurement electrode portion 33 is pushed up from the lower surface side. In that case, the side walls of the substrate layer 20 that configure the measurement flow path 53 are moved in directions away from each other, as indicated by solid-line arrows in FIG. 8. Accordingly, the nano-electrodes 34 are moved in directions away from each other, as indicated by dashed-line arrows in FIG. 8. As a result, the interelectrode distance increases. In this way, the interelectrode distance is adjusted by pushing the electrode substrate 1 upward with the pushing-up device 93.

2. Processing for Measuring Tunneling Current in Biopolymers

Figure 9:
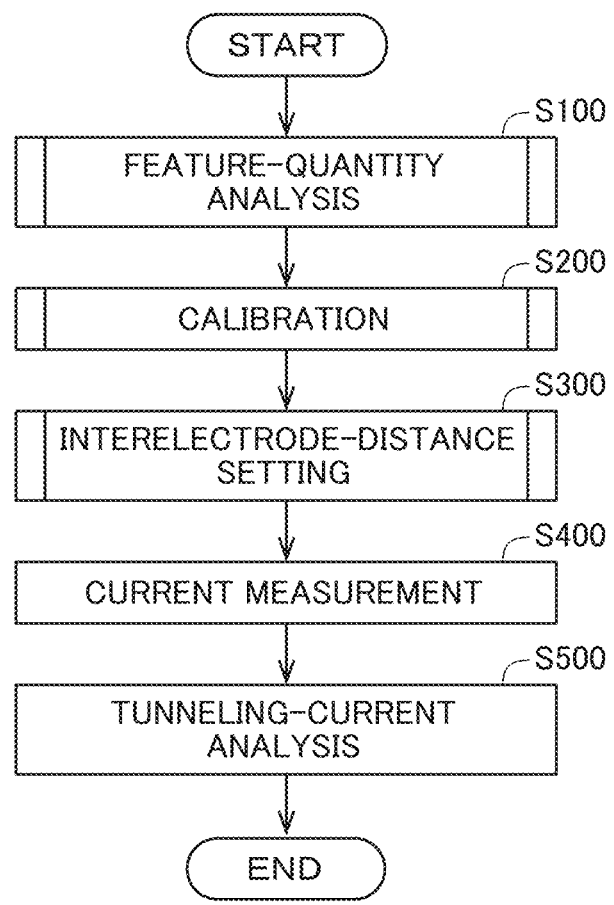
FIG. 9 is a flowchart illustrating a procedure of processing for measuring a tunneling current in biopolymers.

Next, a procedure of processing for measuring a tunneling current in biopolymers, using the electrode substrate 1 and the current measurement apparatus 9, will be described with reference to FIG. 9. FIG. 9 is a flowchart illustrating the procedure of processing for measuring a tunneling current in biopolymers in a liquid sample in which the biopolymers float in a liquid containing an electrolyte. In the present embodiment, the biopolymers contained in the liquid sample are nucleotides. The electrolyte-containing liquid included in the liquid sample is a liquid such as an NaCl solution in which a solute is dissolved in a solvent with a high polarity such as water.

As illustrated in FIG. 9, in the processing for measuring a tunneling current in biopolymers, first, analysis is conducted on a feature quantity for the influence that ions or molecules such as dipoles or organic dipoles in the liquid sample have on the measured current (step S100). Here, a description is given of the behavior of the current flowing between the nano-electrodes 34 when the nano-electrodes 34 are arranged in an electrolyte-containing liquid and a voltage is applied between the nano-electrodes 34.

Figure 10:
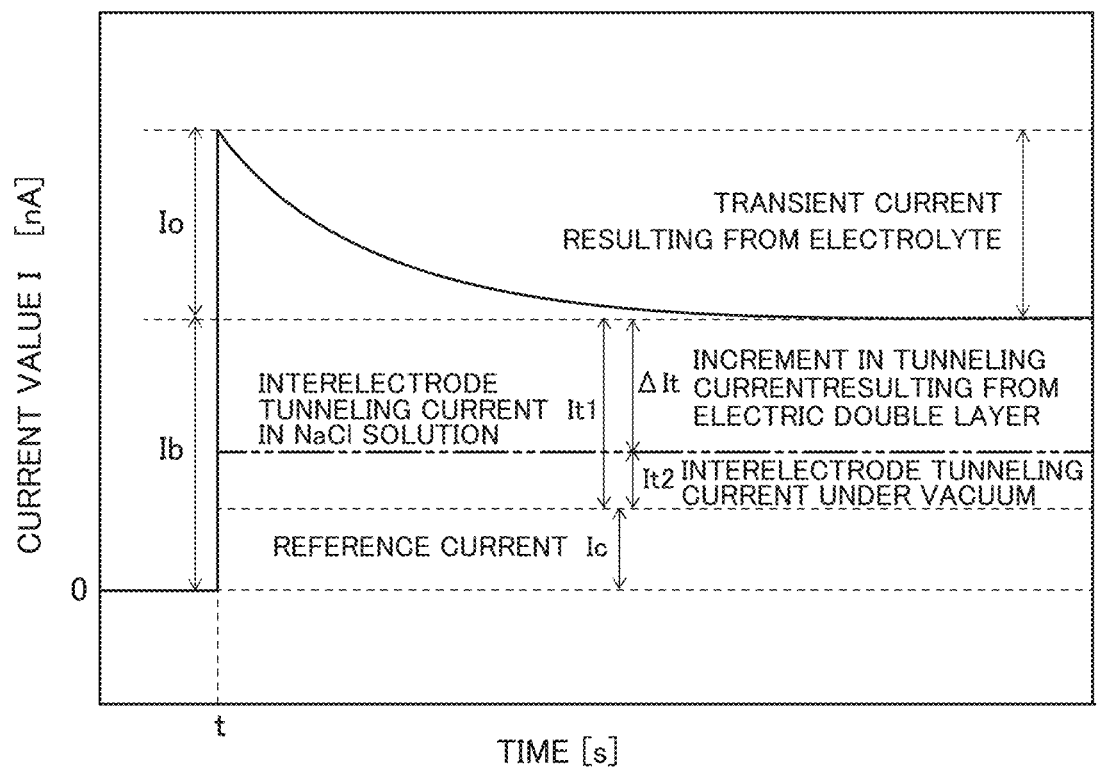
FIG. 10 is a diagram schematically illustrating the behavior of a current flowing between nano-electrodes arranged in an electrolyte-containing liquid.
Figure 11:
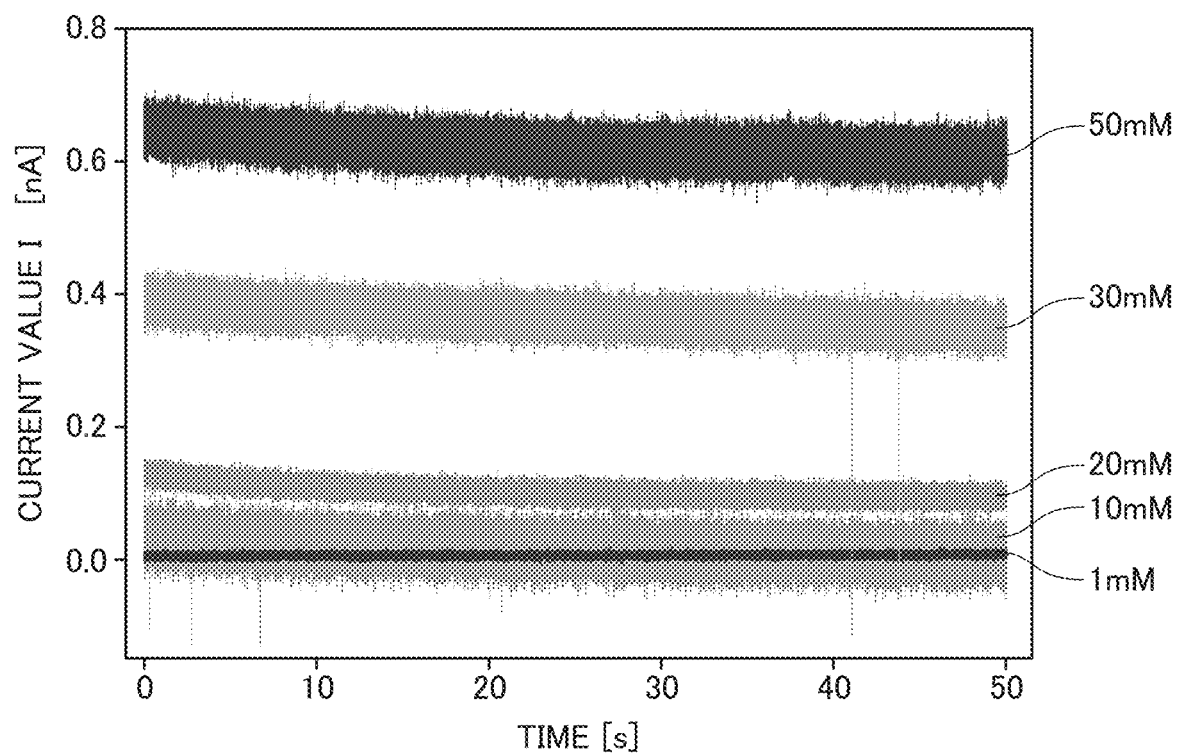
FIG. 11 is a diagram illustrating the behavior of an initial current value when a voltage is applied between nano-electrodes arranged in an NaCl solution.

FIG. 10 is a diagram schematically illustrating the behavior of the current flowing between the nano-electrodes 34 when a predetermined voltage is applied between the nano-electrodes 34 arranged in an electrolyte-containing liquid. FIG. 11 is a diagram illustrating experimental data on the initial current value when a voltage is applied between the nano-electrodes 34 while the nano-electrodes 34 are arranged in different NaCl solutions with a plurality of concentrations.

As illustrated in FIG. 10, when the application of the voltage between the nano-electrodes 34 is started at time t, current as indicated by the solid line in FIG. 10 flows between the nano-electrodes 34. At this time, the current flowing between the nano-electrodes 34 includes a base current Ib that indicates a current value between the nano-electrodes 34 in a steady state and a transient current resulting from the electrolyte contained in the liquid sample. The base current Ib includes a reference current Ic and a tunneling current It1 that flows between the nano-electrodes 34, the reference current Ic resulting from a leakage current, the configuration of the current measurement apparatus 9, and environments around the current measurement apparatus 9. A maximum value of the transient current is assumed to be Io.

When the nano-electrodes 34 are arranged in a vacuum, the aforementioned reference current Ic and a tunneling current It2 between the nano-electrodes 34 flow between the nano-electrodes 34. In this case, current as indicated by the dashed double-dotted line in FIG. 10 flows between the nano-electrodes 34.

In contrast, when the nano-electrodes 34 are arranged in an electrolyte-containing liquid, the application of the voltage between the nano-electrodes 34 causes the reference current Ic and the tunneling current It1 to flow between the nano-electrodes 34 and also causes ions or molecules such as dipoles or organic dipoles in the liquid to move and migrate between the nano-electrodes 34. These motion and migration of ions and molecules temporarily increases the current value between the nano-electrodes 34. This temporary increase in current value corresponds to the transient current.

When the motion and migration of ions and molecules have settled down, an electric double layer is formed in the liquid along the surfaces of the nano-electrodes 34. When current flows between the nano-electrodes 34 via this electric double layer, the tunneling current flowing between the nano-electrodes 34 increases as compared with that in the case where there is no intervention of the electric double layer. Thus, the tunneling current It1 in the electrolyte-containing liquid increases from the tunneling current It2 flowing under vacuum by an increment ΔIt in the tunneling current resulting from the electric double layer.

FIG. 11 illustrates the behavior of the initial current value when a voltage is applied between the nano-electrodes 34, using NaCl solutions with different NaCl concentrations of 1 mM, 10 mM, 20 mM, 30 mM, and 50 mM. When the NaCl concentration is higher than or equal to 10 mM, a transient phenomenon appears markedly in the current value as illustrated in FIG. 11. Ions and molecules forming the solvent and solute, which relate to the formation of the electric double layer, increases in number with increasing concentration of the electrolyte, i.e., NaCl. Thus, the current value after the settle down of the transient phenomenon increases as the concentration of NaCl increases.

In this way, when the nano-electrodes 34 are arranged in the electrolyte-containing liquid and a voltage is applied between the nano-electrodes 34, a transient phenomenon may occur in the current flowing between the nano-electrodes 34. Thus, in the case of changing the voltage applied between the nano-electrodes 34 or in the case of changing the interelectrode distance between the nano-electrodes 34, if any operation or any analysis of the current value is performed without giving consideration to the transient phenomenon, errors will occur in operation content, acquired data, or analysis content.

Even in the case of using the same electrode substrate 1 and the same current measurement apparatus 9, the increment in the tunneling current resulting from the electric double layer differs depending on the type and concentration of the electrolyte in the liquid, which intervenes between the nano-electrodes 34. Therefore, it is necessary to perform the feature-quantity analysis processing in step S100 for each liquid sample to be measured. A specific procedure in step S100 will be described later.

After the feature-quantity analysis processing in step S100 has been performed, processing for calibrating the nano-electrodes 34 (calibration) is performed (step S200). The calibration processing in step S200 includes analyzing a relationship between a voltage Vp applied to the piezo-actuator 942 and a current value I between the nano-electrodes 34, the applied voltage Vp being a manipulated variable for causing the interelectrode distance d between the nano-electrode 34 to fluctuate, and the current value I being detected by the ammeter 96. This enables estimating the relationship between the interelectrode distance d and the applied voltage Vp, which is a manipulated variable for the pair of nano-electrodes 34. A specific procedure in step S200 will be described later.

Then, the interelectrode distance d between the nano-electrodes 34 is set to a desired distance in order to measure the tunneling current in the biopolymers (step S300). A specific procedure in step S300 will be described later.

After the interelectrode distance d between the nano-electrodes 34 has been set to the desired distance, the current value flowing between the nano-electrodes 34 is measured, and the tunneling current in biopolymers is measured (step S400). At this time, the controller 90 may perform feedback control as necessary so that the interelectrode distance d is set to fall within a desired range.

After the tunneling current in the biopolymers has been measured in step S400, acquired current data is analyzed (step S500). Single molecules forming biopolymers have a unique tunneling current value depending on the type. Thus, a sequence of single molecules in biopolymers can be estimated by analyzing current data on the tunneling current in the biopolymers flowing in the liquid sample and passing through between the nano-electrodes 34.

3. Feature-Quantity Analysis Processing

Figure 12:
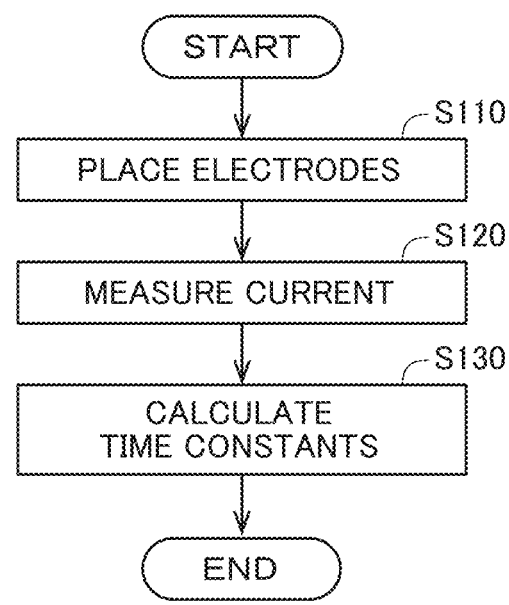
FIG. 12 is a flowchart illustrating a procedure of feature-quantity analysis processing.

Next, the feature-quantity analysis processing in step S100 will be described with reference to FIG. 12. FIG. 12 is a flowchart illustrating a procedure of the feature-quantity analysis processing.

In the feature-quantity analysis processing, first, the nano-electrodes 34 are arranged in a liquid sample such that the interelectrode distance d between the nano-electrodes 34 become greater than zero (step S110). In order to confirm that the interelectrode distance d is not zero, i.e., the tip portions of the two nano-electrodes 34 are not in contact with each other, a voltage may be applied between the nano-electrodes 34 to confirm that the current value I of the current flowing between the nano-electrodes 34 is smaller than a predetermined voltage value. In that case, after the confirmation of the current value I, the application of the voltage to the nano-electrodes 34 is stopped and some standby time is provided.

Thereafter, a predetermined voltage is applied between the nano-electrodes 34, with the nano-electrodes 34 having a fixed interelectrode distance. Then, the current value I between the nano-electrodes 34 is measured for a predetermined period of time from the start of the application of the voltage (step S120). The current value I obtained at this time exhibits transient response characteristics as illustrated in FIG. 11. In the step of measuring current in step S120, biopolymers may pass through between the nano-electrodes 34. In that case, the obtained current value I may sometimes include a signal that appears when biopolymers have passed through between the nano-electrodes 34.

Then, the obtained current data is analyzed to calculate a time constant, which is a feature quantity (step S130). The calculated time constant represents a duration of time until when the transient phenomenon caused based on the changes in the applied voltage and the interelectrode distance d between the nano-electrodes 34 converges and for the amount of change resulting from the transient phenomenon to reduce to approximately 36.2%. The feature quantity calculated in the present invention is not limited to the time constant. The feature quantity to be calculated may be any other parameter as long as the parameter represents the condition of convergence of the transient phenomenon.

The transient phenomenon of the current value I between the nano-electrodes 34 as illustrated in FIG. 10 can be expressed by Expression (1) below, using the base current Ib, which is the current value between the nano-electrodes 34 in the steady state, and a maximum value Io of a transient current component. Note that the base current Ib is superposition of the aforementioned reference current Ic and the value of the tunneling current flowing between the nano-electrodes 34 via the electrolyte-containing liquid included in the liquid sample.

[Math. 1]

$$I(t) = Ib + Io \cdot e^{-\frac{t}{\tau}} \quad (1)$$

The second term of the right-hand side of Expression (1) represents a transient current component, where r is a time constant of the transient current component. Since the current value I between the nano-electrodes 34 can be approximated by Expression (1), the time constant τ of the transient phenomenon can be calculated by approximating the current data obtained in step S110 by Expression (1). The time constant τ is used as the feature quantity of the transient phenomenon in subsequent processing including the calibration processing, interelectrode-distance setting processing, and current measurement processing. In each of the subsequent processing, it is possible, by performing the processing using the time constant τ in consideration of the transient phenomenon, to reduce the occurrence of errors in operation content, acquired data, or analysis content resulting from the transient phenomenon caused in each of the processing.

Here, an analysis of real current-value data shows that the current value I between the nano-electrodes 34 includes a plurality of transient current components superposed. In view of this, in the present embodiment, the current value I between the nano-electrodes 34 is approximated by Expression (2) below, assuming that five types of transient current components are superposed.

[Math. 2]

$$I(t) = Ib + \sum_{n=1}^{5} In \cdot e^{-\frac{t}{\tau_n}} \quad (2)$$

The second term of the right hand side of Expression (2) represents a sum of the five transient current components, where n=1 to 5. Each of the five transient current components have a maximum current component In and a time constant τn, where n=1 to 5. That is, the five transient current components respectively have maximum current components 11, 12, 13, 14, and 15 and time constant τ1, τ2, τ3, τ4, and τ5. In the following description, the values of the five time constants τ1 to τ5 are in ascending order from τ1 to τ5.

In the present embodiment, five time constants are calculated, but the present invention is not limited to this example. The number of time constants to be calculated may be in the range of 1 to 4, or may be six or more. As described above, a plurality of transient current components are superposed on the current value I between the nano-electrodes 34. Thus, in order to more accurately exclude the influence of a plurality of transient current components appearing in the current value I, it is preferable that three or more transient current components are taken into consideration. If the number of time constants to be calculated is too large, even the time constant of a transient current component that has little influence on the measurement of the current value between the nano-electrodes 34 may be calculated, or even a transient current component that actually does not occur may be calculated. Accordingly, the number of time constants to be calculated is preferably in the range of 3 to 6.

4. Electrode-Pair Calibration Processing

Figure 13:
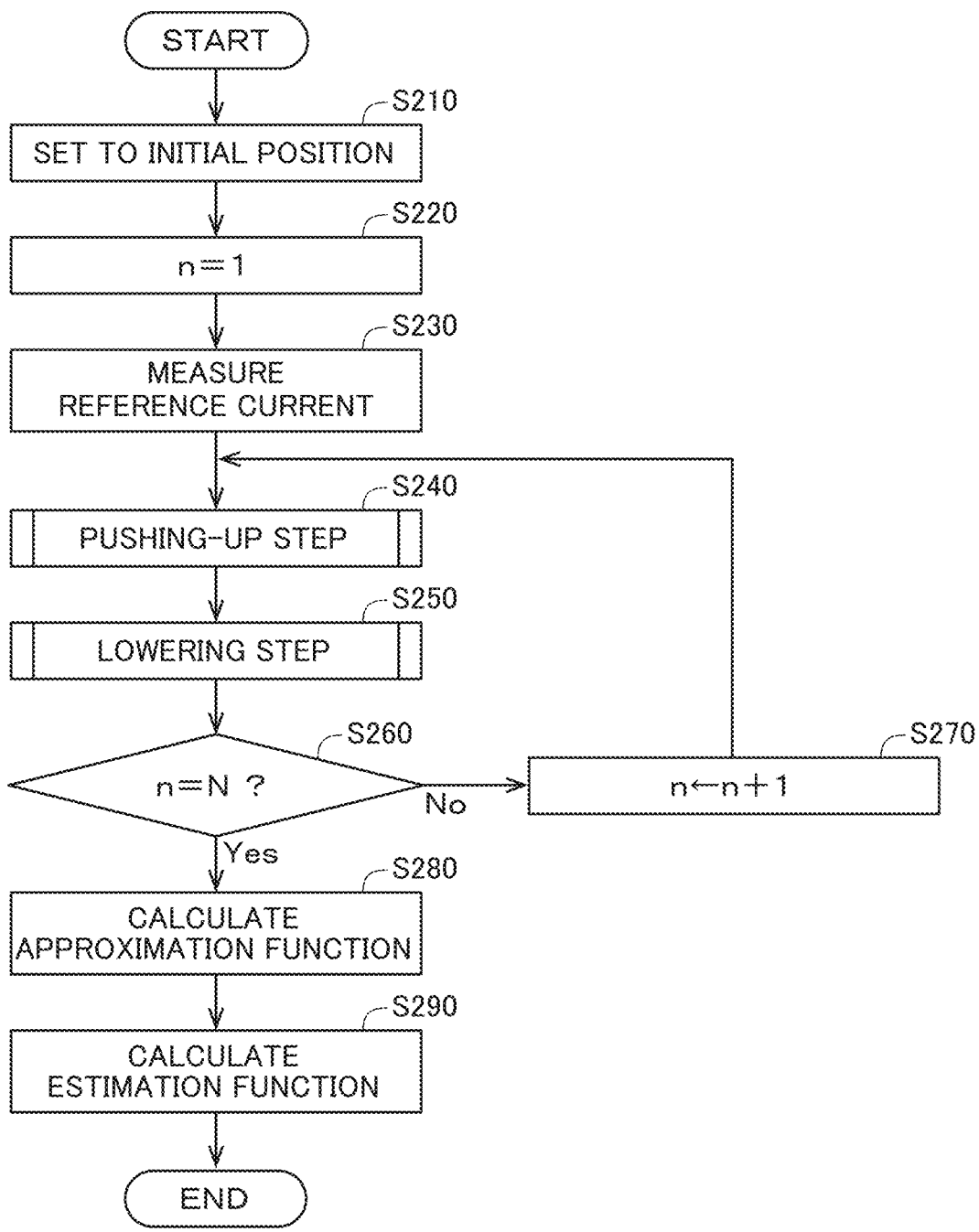
FIG. 13 is a flowchart illustrating a procedure of nano-electrode calibration processing.

Next, the processing for calibrating the nano-electrodes 34 in step S200 will be described with reference to FIG. 13. FIG. 13 is a flowchart illustrating a procedure of the processing for calibrating the nano-electrodes 34.

In the processing for calibrating the nano-electrodes 34, the amount of pushing up the electrode substrate 1 with the pushing-up device 93 is changed to change the interelectrode distance d and measure the current value I of the current flowing between the nano-electrodes 34 during that period of time. Then, the relationship between a manipulated variable of the pushing-up device 93 and the interelectrode distance d is estimated from the relationship between the manipulated variable and the current value I.

In the calibration processing according to the present embodiment, the pushing up and pulling back of the electrode substrate 1 with the pushing-up device 93 are repeated to change the interelectrode distance d between the nano-electrodes 34 and to acquire the value of the tunneling current flowing between the nano-electrodes 34 during that period of time.

In the calibration processing, first, the electrode substrate 1 is arranged in the current measurement apparatus 9 and set at the initial position (step S210). Then, the controller 90 sets a count n to 1 (step S220).

Then, the controller 90 measures the reference current Ic (step S230). Specifically, the controller 90 pushes the pushing-up device 93 up, and measures the current value of the current flowing between the nano-electrodes 34 while keeping the interelectrode distance d large enough so as not to produce a flow of the tunneling current between the nano-electrodes 34. Accordingly, it is possible to measure the reference current Ic resulting from factors including a leakage current, the configuration of the current measurement apparatus 9, and environments around the current measurement apparatus 9.

In the case of measuring the reference current Ic, the controller 90 waits until the elapse of a predetermined initial standby time t0 after the distance between the nano-electrodes 34 has reached a distance at which the reference current Ic can be measured, and then measures the reference current Ic. This initial standby time to is calculated based on the time constant τ5 having the largest value among the five time constants τ1 to τ5 calculated in the feature-quantity analysis processing in step S100. For example, the initial standby time t0 may be calculated by multiplying the time constant τ5 by a predetermined real number.

In this way, the measurement timing of measuring the reference current Ic is determined based on the time constant τ5, which is the feature quantity. This reduces the occurrence of errors in the measured value, which may be caused by the influence of the transient phenomenon, in the case of measuring the reference current Ic. After the measurement of the reference current Ic, the controller 90 lowers the pushing-up device 93 to a predetermined position.

After having lowered the pushing-up device 93 to the predetermined position, the controller 90 performs a step of pushing up the electrode substrate 1 with the pushing-up device 93 (step S240). That is, the controller 90 performs an operation in a direction of increasing the interelectrode distance d between the nano-electrodes 34.

The position of the pushing-up device 93 at the start of the pushing-up step may be a position in which the tip portions of the nano-electrodes 34 are in contact with each other or may be a position in which the tip portions of the nano-electrodes 34 are spaced from each other, as long as the current value measured at that position by the ammeter 96 becomes larger than a first threshold value, which will be described later.

In the pushing-up step in step S240 and a lowering step in step S250 described later, the pushing up and lowering of the pushing-up device 93 are implemented by increasing or decreasing the voltage Vp applied to the piezo-actuator 942. Thus, the manipulated variable used to push up and lower the pushing-up device 93 is the voltage value of the voltage Vp applied to the piezo-actuator 942. As the voltage value of the applied voltage Vp increases, the amount of pushing up with the pushing-up device 93 increases and the interelectrode distance d increases. On the other hand, as the voltage value of the applied voltage Vp decreases, the amount of pushing up with the pushing-up device 93 decreases and the interelectrode distance d decreases.

Figure 14:
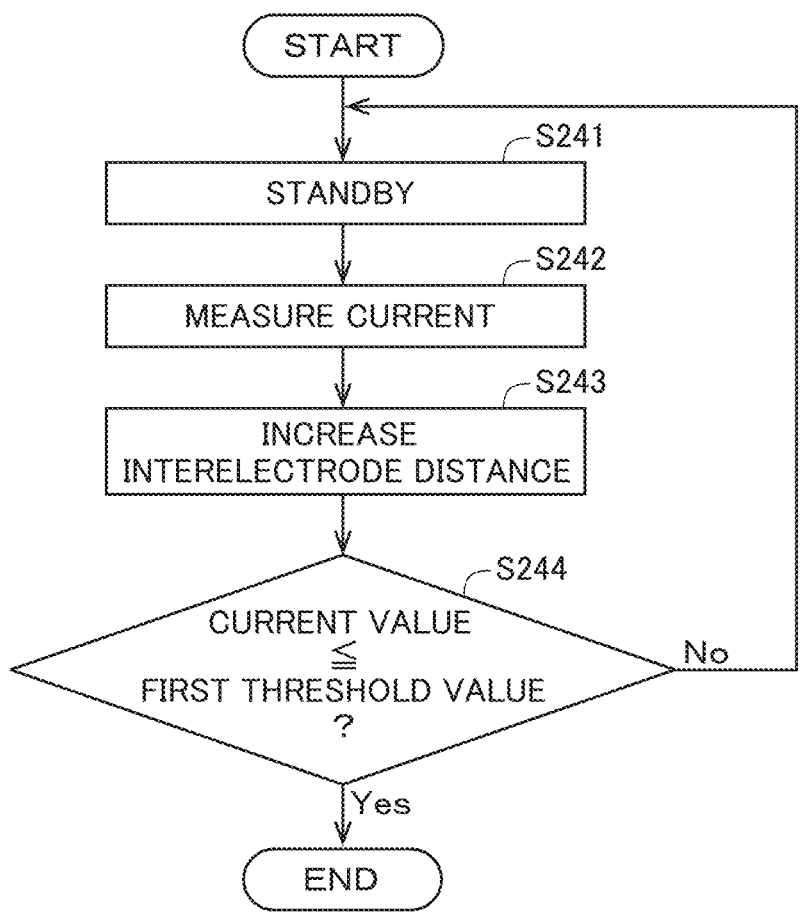
FIG. 14 is a flowchart illustrating a specific procedure of a pushing-up step.

The pushing-up step in step S240 is performed until the current value measured by the ammeter % becomes lower than or equal to a predetermined first threshold value. FIG. 14 is a flowchart illustrating a specific procedure of the pushing-up step in step S240.

As illustrated in FIG. 14, in step S240, the controller 90 first stands by for a predetermined standby time (step S241). In this way, the controller 90 waits until the influence of the transient phenomenon associated with the change in the interelectrode distance d that has been made immediately before the standby step in step S241 becomes small enough. This reduces the occurrence of errors in the measured current value, resulting from the transient phenomenon, during current measurement in the subsequent step S242.

The standby time in the first iteration of step S241 may, for example, be the same initial standby time t0 as that in the case of measuring the reference current Ic in step S230. The standby time in the second and subsequent iterations of step S241 is a predetermined first standby time t1. This first standby time t1 is calculated based on the time constant τ1 having the smallest value among the five time constants τ1 to τ5 calculated in the feature-quantity analysis processing in step S100. For example, the first standby time t1 may be calculated by multiplying the time constant τ1 by a predetermined real number. Alternatively, the first standby time t1 may also be calculated based on any of the other time constants τ2 to τ5.

As described above, the standby time in the first iteration of step S241 is preferably longer than the standby time in the second iteration of step S241. This is because the amount of change in the interelectrode distance d before the start of the first iteration of step S241 is greater than the amount of change in the interelectrode distance d before the start of the second and subsequent iterations of step S241. Note that the standby time in the first iteration of step S241 is not limited to the same initial standby time t0 as that in the case of measuring the reference current Ic in step S230, and may be any other standby time calculated by other methods as long as the standby time is longer than or equal to the first standby time t1, which is the standby time in the second iteration of step S241.

Next, the controller 90 stores the voltage value of the voltage Vp applied to the piezo-actuator 942 and the current value measured by the ammeter 96 at that time (step S242). That is, the controller 90 acquires the value of the manipulated variable used to change the interelectrode distance d and the current value between the nano-electrodes 34.

Then, the controller 90 increases the applied voltage Vp by a predetermined amount to increase the interelectrode distance d (step S243). That is, the controller 90 changes the manipulated variable used to change the interelectrode distance d to change the interelectrode distance d.

After having changed the interelectrode distance d, the controller 90 determines whether the current value measured by the ammeter 96 is less than or equal to the predetermined first threshold value (step S244). When the current value measured by the ammeter 96 is greater than the first threshold value (No in step S244), the controller 90 returns to step S241 and repeats the standby step, the current-value measurement step, and the step of increasing the interelectrode distance d. On the other hand, when the current value measured by the ammeter 96 is less than or equal to the first threshold value (Yes in step S244), the controller 90 ends the pushing-up step in step S240.

When the pushing-up step in step S240 has ended, then the controller 90 performs the step of lowering the pushing-up device 93 (step S250). That is, the controller 90 performs an operation in a direction of reducing the interelectrode distance d between the nano-electrodes 34.

Figure 15:
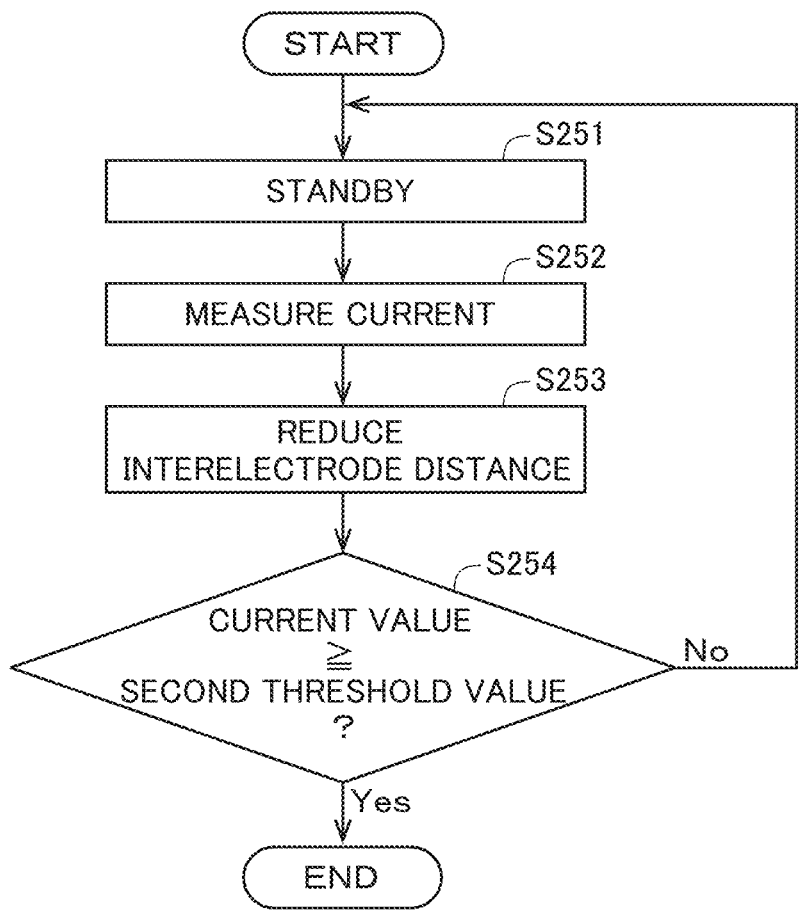
FIG. 15 is a flowchart illustrating a specific procedure of a lowering step.

The lowering step in step S250 is performed until the current value measured by the ammeter 96 becomes greater than or equal to a predetermined second threshold value. FIG. 15 is a flowchart illustrating a specific procedure of the lowering step in step S250.

As illustrated in FIG. 15, in step S250, the controller 90 first stands by for a predetermined first standby time t1 (step S251). This first standby time t1 is the same as the standby time in the second and subsequent iterations of step S241.

Next, the controller 90 stores the voltage value of the voltage Vp applied to the piezo-actuator 942 and the current value measured by the ammeter 96 at that time (step S252). That is, the controller 90 acquires the value of the manipulated variable used to change the interelectrode distance d and the current value I between the nano-electrodes 34.

Then, the controller 90 reduces the applied voltage Vp by a predetermined amount to reduce the interelectrode distance d (step S253). That is, the controller 90 changes the manipulated variable used to change the interelectrode distance d to change the interelectrode distance d.

After having changed the interelectrode distance d, the controller 90 determines whether the current value measured by the ammeter 96 is greater than or equal to the predetermined second threshold value (step S254). When the current value measured by the ammeter 96 is less than the second threshold value (No in step S254), the controller 90 returns to step S251 and repeats the standby step, the current-value measurement step, and the step of reducing the interelectrode distance d. On the other hand, when the current value measured by the ammeter 96 is greater than or equal to the second threshold value (Yes in step S254), the controller 90 ends the lowering step in step S250.

Then, the controller 90 determines whether the count n has reached a predetermined repetition count N (step S260). When the count n has not reached the repetition count N (No in step S260), the controller 90 proceeds to step S270 and increments the count n. Thereafter, the controller 90 returns to step S240 and again performs the step of pushing up the pushing-up device 93 and the step of lowering the pushing-up device 93. On the other hand, when the count n has reached the repetition count N (Yes in step S260), the controller 90 proceeds to step S280.

In this way, in the pushing-up step in step S240 and the lowering step in step S250, the operation of changing the interelectrode distance d is performed while applying a predetermined voltage between the nano-electrodes 34, and the current value I between the nano-electrodes 34 is acquired. At this time, the pushing-up step in step S240 and the lowering step in step S250 are repeatedly performed a plurality of times, so that an approximation function described later can be obtained more accurately.

Figure 16:
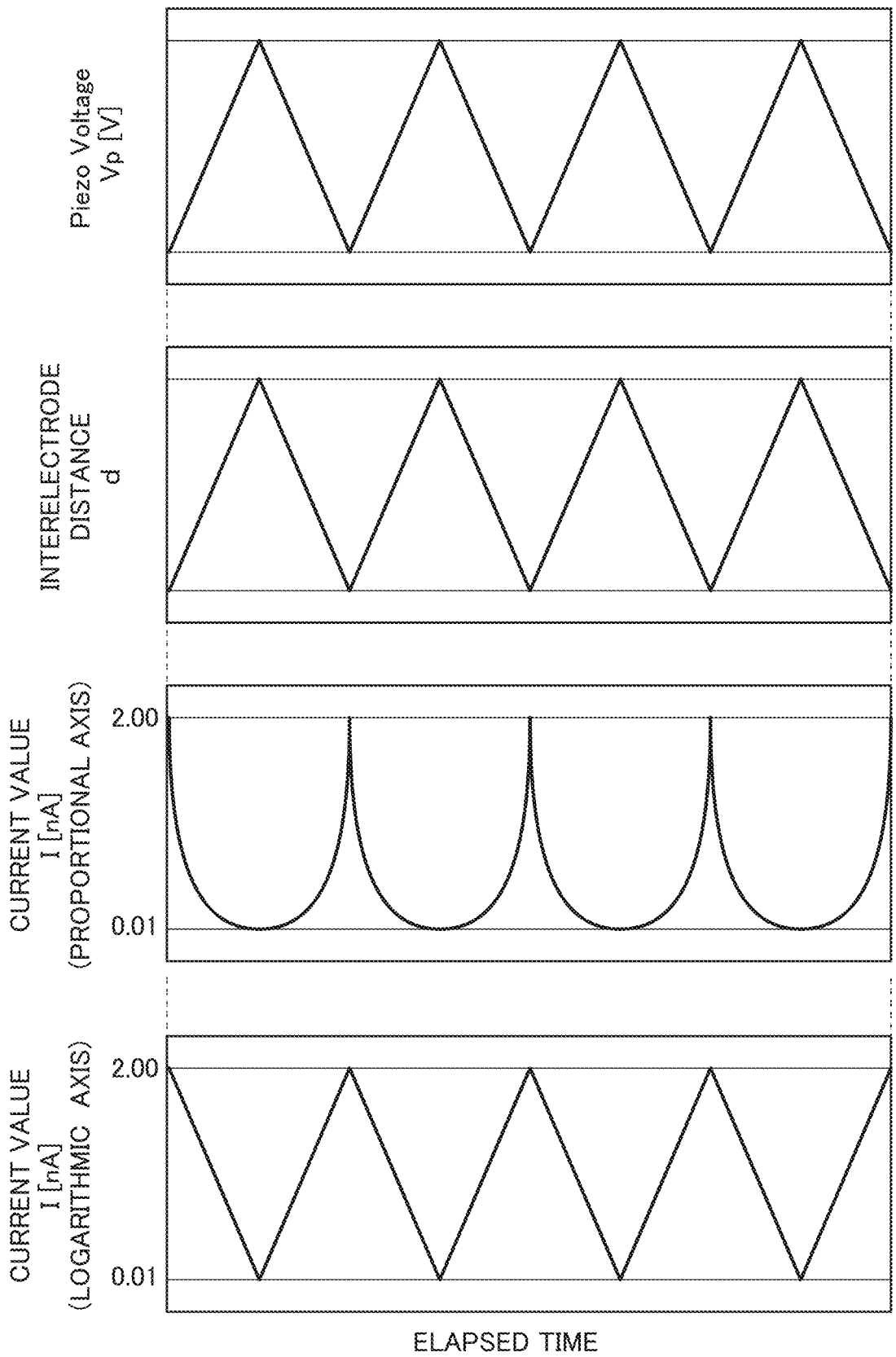
FIG. 16 is a diagram schematically illustrating changes over time in applied voltage and current value in the nano-electrode calibration processing.

FIG. 16 is a diagram schematically illustrating changes over time in the voltage Vp applied to the piezo-actuator 942 and the current value between the nano-electrodes 34 in the processing of calculating the nano-electrodes 34. In FIG. 16, the first section is an illustration of the voltage Vp applied to the piezo-actuator 942, the second section is an illustration of the interelectrode distance d between the nano-electrodes 34, the third section is an illustration of the change over time in the current value I between the nano-electrodes 34 detected by the ammeter 96, plotted on the proportional axis, and the fourth section is an illustration of the change over time in the current value between the nano-electrodes 34 detected by the ammeter 96, plotted on the logarithm axis. In order to facilitate understanding of the relationship of these values, the standby steps in steps S241 and S251 are not illustrated in FIG. 16.

In the present embodiment, the first threshold value is 0.01 nA and the second threshold value is 2.00 nA as illustrated in the third and fourth sections in FIG. 16. The first threshold value is set to a larger value than the reference current Ic. The second threshold value is set to a value larger than the first threshold value and smaller than the current value flowing in the case where the nano-electrodes 34 are in contact with each other.

As described above, the manipulated variable used to push and lower the pushing-up device 93 in steps S240 and S250 of the present embodiment is the voltage Vp applied to the piezo-actuator 942. In the piezo-actuator 942 according to the present embodiment, the applied voltage Vp is roughly proportional to the amount of pushing up. The amount of pushing up is also roughly proportional to the interelectrode distance d. Thus, the amount of change in the voltage value of the applied voltage Vp is roughly proportional to the amount change in the interelectrode distance d. Here, the relationship between the interelectrode distance d and the applied voltage Vp is expressed by Expression (3) below, where α is a proportionality factor.

[Math. 3]

$$d = \alpha \cdot Vp \tag{3}$$

In step S240, the applied voltage Vp is gradually increased as illustrated in FIG. 16. Specifically, the applied voltage Vp is increased by a predetermined amount every time step S243 is executed. Thus, the interelectrode distance d also increases with increasing applied voltage Vp. In step S250, the applied voltage Vp is gradually reduced as illustrated in FIG. 16. Specifically, the applied voltage Vp is reduced by a predetermined amount every time step S253 is executed. Thus, the interelectrode distance d decreases by an approximately constant ratio in step S250.

Meanwhile, the interelectrode distance d and the tunneling current It flowing between the electrodes have a relationship as expressed by Expression (4) below, where K is a constant and β is a known constant.

[Math. 4]

$$It = K \cdot \exp(-\beta \cdot d) \tag{4}$$

On the other hand, the current value I measured by the ammeter 96 is a value obtained by adding the reference current Ic and the tunneling current It, and therefore the current value I is expressed by Expression (5) below.

[Math. 5]

$$I = Ic + It = Ic + K \cdot \exp(-\beta \cdot d) \tag{5}$$

Thus, in step S240, the current value I decreases exponentially as the pushing-up device 93 is gradually pushed up, as illustrated in FIG. 16. In step S250, the current value I increases exponentially as the pushing-up device 93 is gradually pulled back.

When the procedure proceeds from step S260 to step S280, the controller 90 calculates an approximation function by approximating the relationship between the manipulated variable used with the pushing-up device 93 and the current value I measured by the ammeter 96 in steps S240 and S250, which are repeatedly performed N times (step S280).

Figure 17:
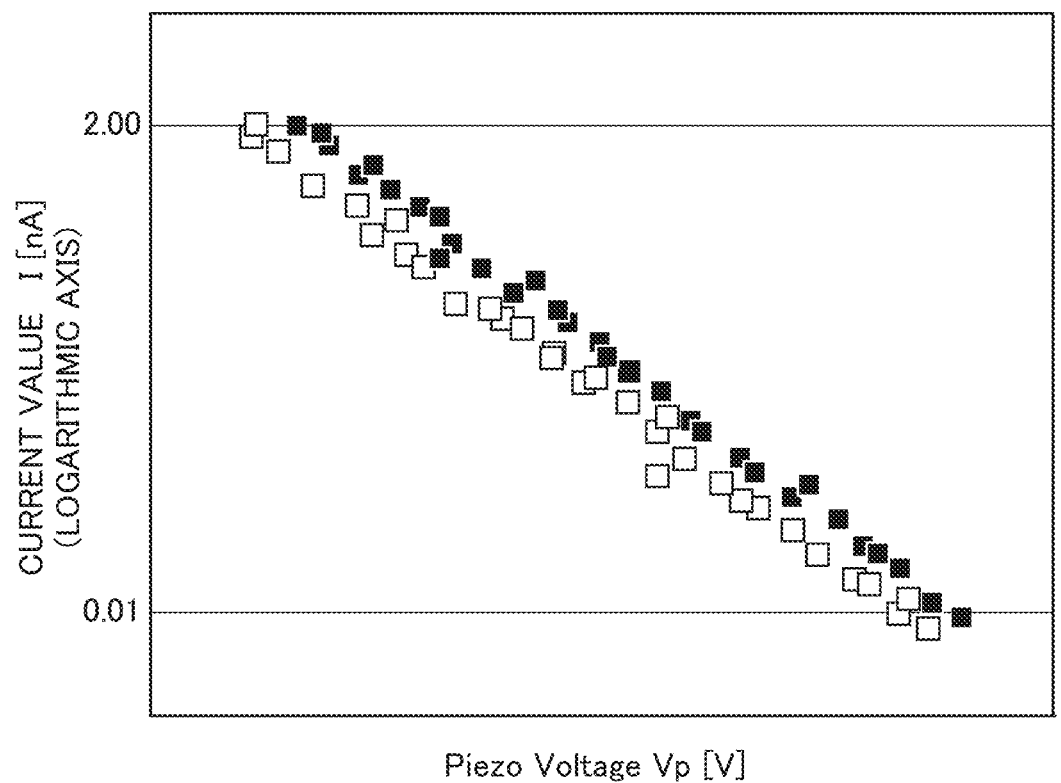
FIG. 17 is a diagram showing one example of measurement data on the applied voltage and the current value in the calibration processing.
Figure 18:
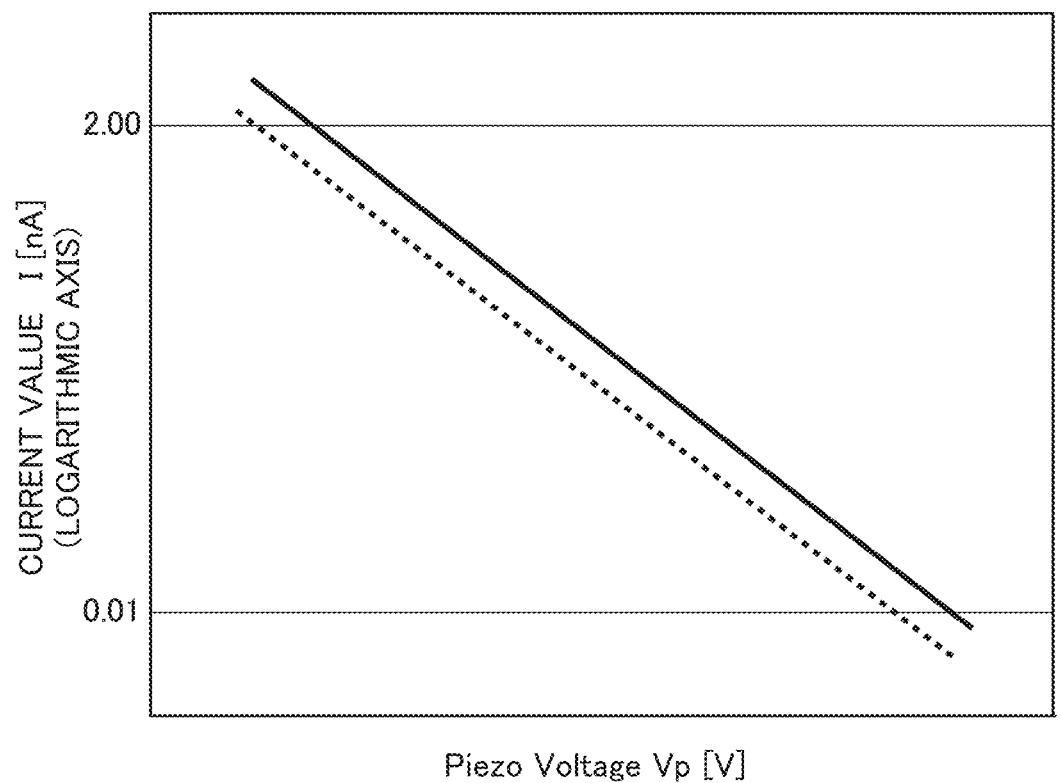
FIG. 18 is a diagram illustrating approximation functions of the measurement data on the applied voltage and the current value in the calibration processing.

FIG. 17 is a diagram showing one example of measurement data on the applied voltage Vp and the current value I in the calibration processing. FIG. 18 is a diagram illustrating the approximation function of the measurement data in the example in FIG. 17. FIGS. 17 and 18 both show semilogarithmic graphs using the axis of real numbers as the horizontal axis and a logarithm axis as the vertical axis. In FIG. 17, black data points represent measurement data in the pushing-up step (step S240), whereas white data points represent measurement data in the lowering step (step S250). In steps S240 and S250, the applied voltage Vp and the measured current value I are stored at predetermined time intervals (e.g., 50 msec).

As illustrated in FIG. 17, the applied voltage Vp and the current value I in steps S240 and S250 have such a relationship that the current value I decreases exponentially as the applied voltage Vp increases. In step S280, this relationship is used to calculate an approximate expression like Expression (6) below and to calculate constants A, B, and C.

[Math. 6]

$$I = A \cdot \exp(-B \cdot Vp) + C \tag{6}$$

In this way, each value is obtained as expressed by Expressions (7) to (9).

[Math. 7]

$$K = A \tag{7}$$

[Math. 8]

$$-\beta \cdot d = -B \cdot Vp \tag{8}$$

[Math. 9]

$$Ic = C \tag{9}$$

Through the above processing, the proportionality factor α for the interelectrode distance d and the applied voltage Vp is obtained as Expression (10) below. This proportionality factor α is a characteristic value obtained for each electrode substrate 1.

[Math. 10]

$$\alpha = \frac{d}{Vp} = \frac{B}{\beta} \tag{10}$$

The calculated proportionality factor α is substituted into Expression (3) to calculate an estimation function that indicates the estimated relationship of the applied voltage Vp, i.e., the manipulated variable, and the interelectrode distance d (step S290). Using the proportionality factor α and the estimation function, the current measurement processing described below is performed.

Through this calibration processing (step S200), the relationship of the manipulated variable (applied voltage Vp) and the interelectrode current value (current value I) is obtained for the pair of nano-electrodes 34. The above-described calibration processing is performed in the liquid sample itself to be measured or in the electrolyte-containing liquid, which is a liquid component of the liquid sample. Thus, the standby steps in steps S241 and S251 are executed in consideration of the transient phenomenon such as the electric double layer. This suppresses the occurrence of errors in current value, resulting from the transient phenomenon.

In the present embodiment, the approximation function for the measurement data in the pushing-up step in step S240 and the approximation function for the measurement data in the lowering step in step S250 are calculated separately in the approximation-function calculation step in step S280. In the estimation-function calculation step in step S290 as well, the estimation function at the time of pushing-up the pushing-up device 93 and the estimation function at the time of lowering the pushing-up device 93 are calculated separately.

In the pushing-up step and the lowering step, the relationship between the applied voltage Vp and the current value I exhibits hysteresis resulting from, for example, hysteresis in the voltage Vp applied to the piezo-actuator 942 and the amount of movement of the piezo-actuator 942. Thus, it is preferable as in the present embodiment that the approximation function and the estimation function in the pushing-up step and the approximation function and the estimation function in the lowering step are respectively calculated separately.

5. Interelectrode-Distance Setting Processing

Figure 19:
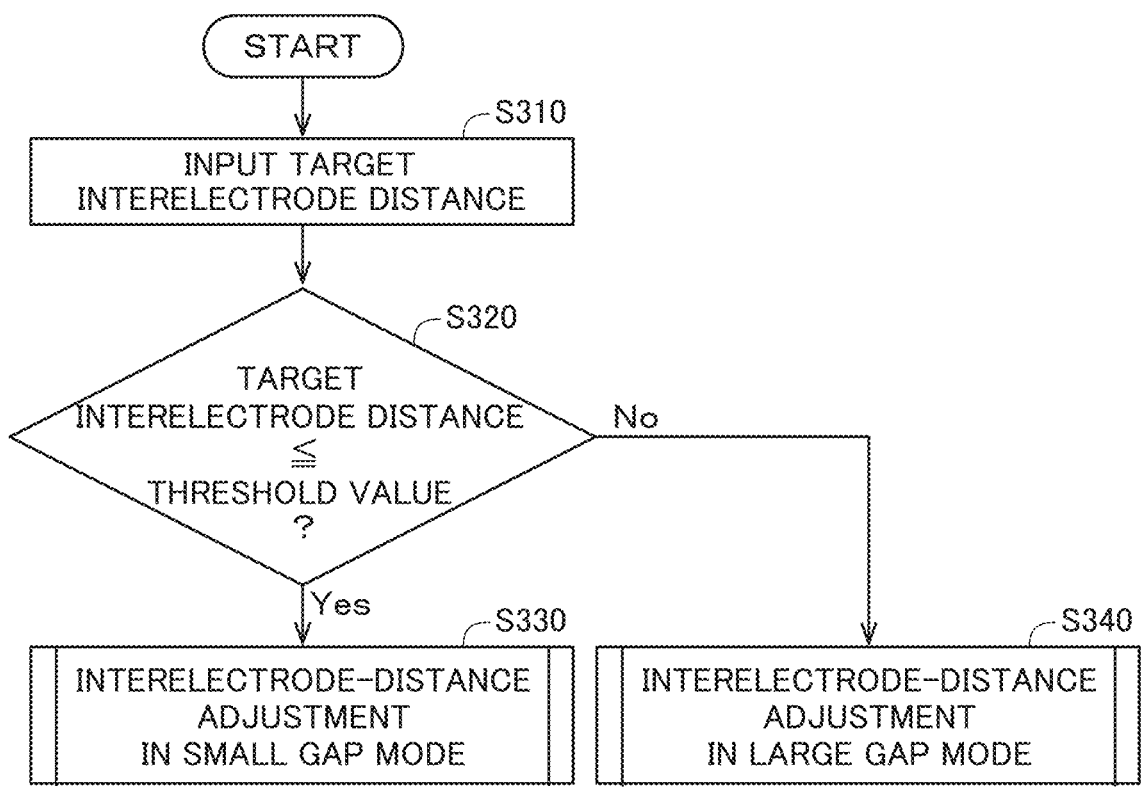
FIG. 19 is a flowchart illustrating a procedure of inter-electrode-distance setting processing.
Figure 20:
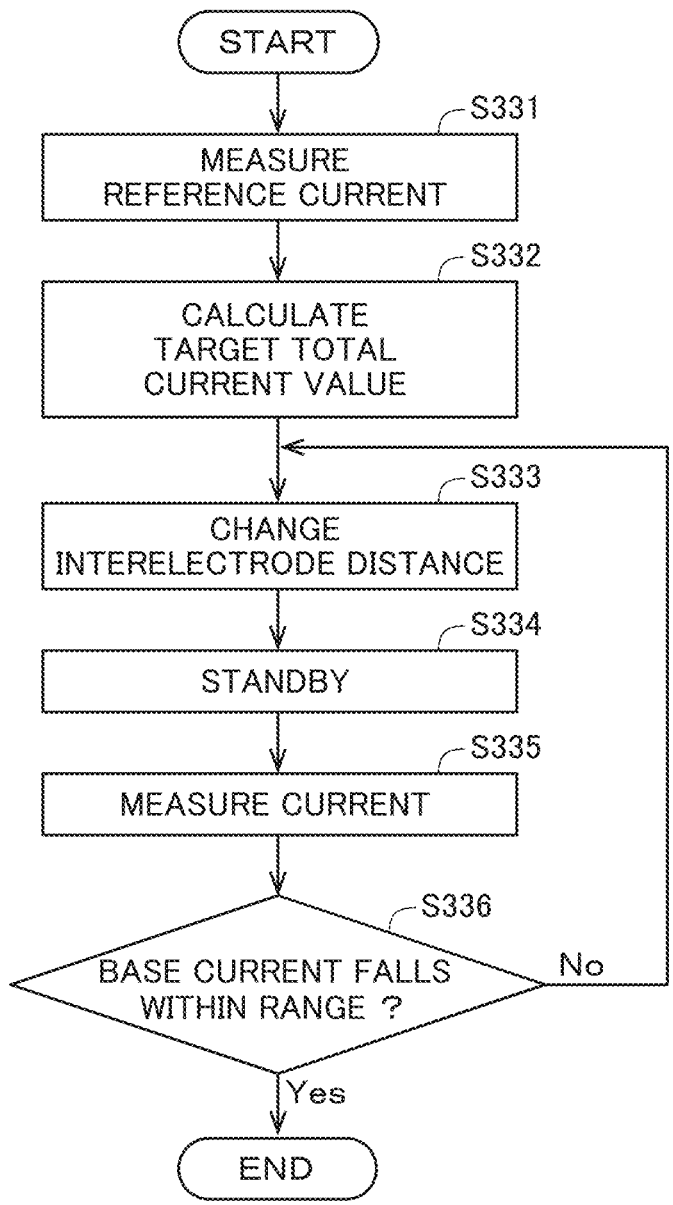
FIG. 20 is a flowchart illustrating a procedure of an interelectrode-distance adjustment step performed in a small gap mode.
Figure 21:
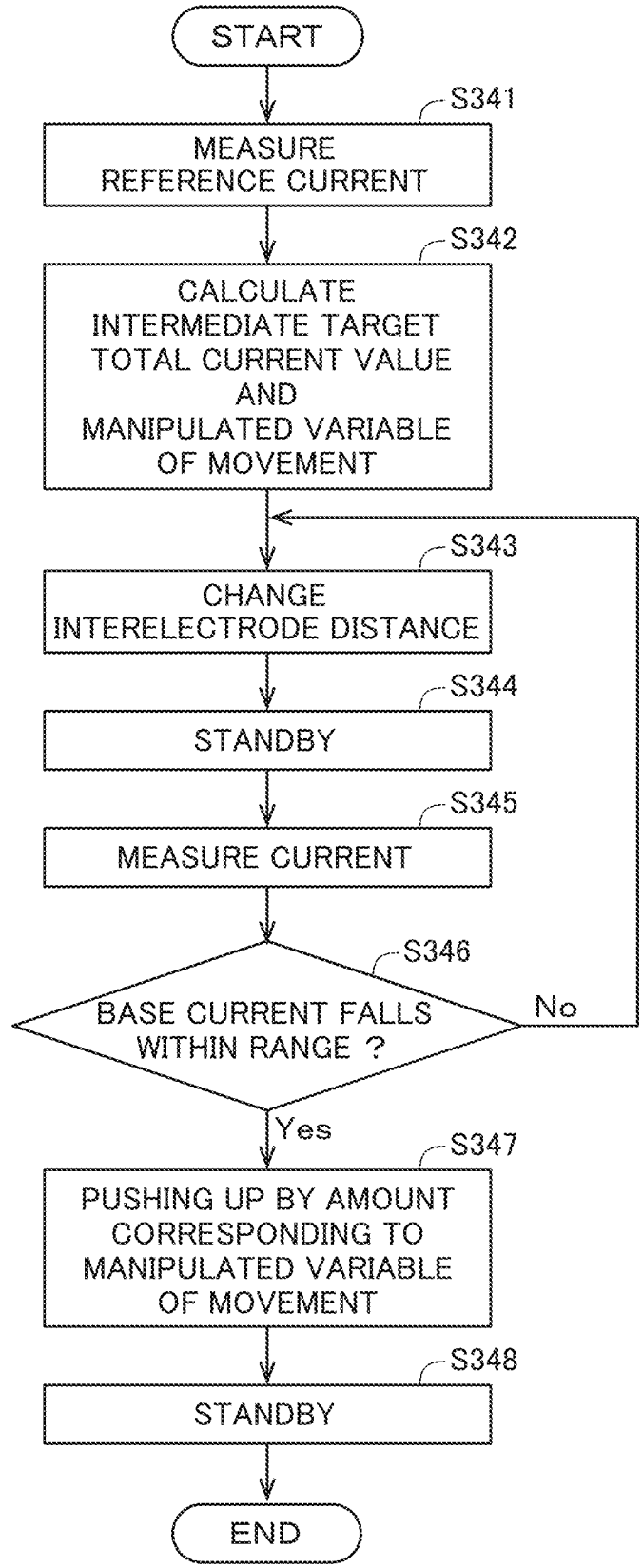
FIG. 21 is a flowchart illustrating a procedure of an interelectrode-distance adjustment step performed in a large gap mode.

Next, processing for setting the interelectrode distance d in order to perform the processing for measuring the current in biopolymers using the electrode substrate 1 will be described with reference to FIGS. 19 to 21. FIG. 19 is a flowchart illustrating a procedure of the interelectrode-distance setting processing in step S300. FIG. 20 is a flowchart illustrating a procedure of an interelectrode-distance adjustment step performed in a small gap mode. FIG. 21 is a flowchart illustrating a procedure of an interelectrode-distance adjustment step performed in a large gap mode.

In the case of measuring the tunneling current in biopolymers, it becomes important to make the measurement with an appropriate interelectrode distance. An appropriate interelectrode distance differs depending on each biopolymer to be measured. This current measurement processing is performed in a liquid sample containing biopolymers to be measured. As illustrated in FIG. 19, in the measurement processing, first, the controller 90 receives, from an external source, input of a target interelectrode distance that is an interelectrode distance aimed to be achieved (step S310). Note that the target interelectrode distance may be input in advance.

Next, the controller 90 determines whether the target interelectrode distance input in step S310 is less than or equal to a predetermined threshold value (step S320). This threshold value is set such that, when the interelectrode distance is equal to the threshold value, the tunneling current value between the nano-electrodes 34 becomes larger than the noise component included in the base current Ib.

In step S320, it may also be determined whether a target tunneling current value Iu that corresponds to the desired target interelectrode distance is greater than or equal to a predetermined threshold value. In that case, for example, the target tunneling current value Iu may be calculated from Expression (4) described previously.

When it is determined in step S320 that the target interelectrode distance is less than or equal to the threshold value (Yes in step S320), the controller 90 proceeds to the interelectrode-distance adjustment step in the small gap mode in step S330. On the other hand, when it is determined that the target interelectrode distance is greater than the threshold value (No in step S320), the controller 90 proceeds to the interelectrode-distance adjustment step in the large gap mode in step S340. In steps S330 and S340, the application of a predetermined voltage to the nano-electrodes 34 continues in order to measure the current between the nano-electrodes 34.

Next, a procedure of the interelectrode-distance adjustment step in the small gap mode will be described with reference to FIG. 20. First, the reference current Ic is measured while the interelectrode distance is increased enough in order not to produce a flow of the tunneling current between the nano-electrodes 34 (step S331). After the measurement of the reference current Ic, the pushing-up device 93 is returned to the position in which the tip portions of the nano-electrodes 34 are in contact with each other.

Figure 22:
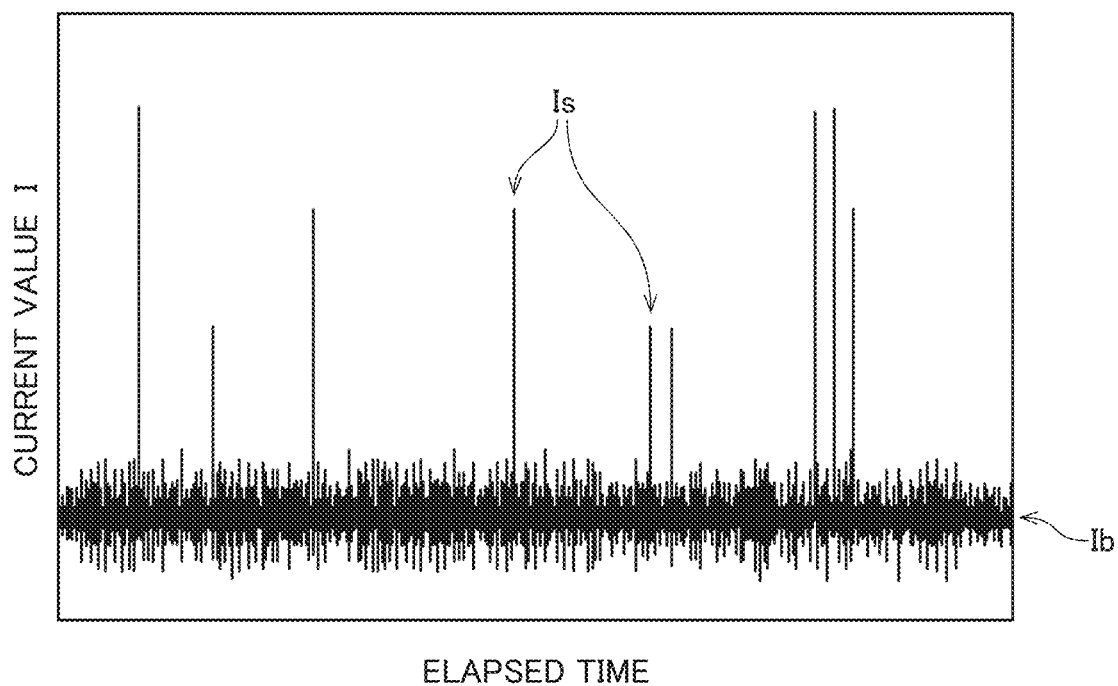
FIG. 22 is a diagram showing one example of a change over time in measured current value.

The reference current Ic is measured by extracting the base current Ib from the current value I measured by the ammeter 96 in step S331. FIG. 22 is a diagram showing one example of a change over time in the measured current value I. As illustrated in FIG. 22, in the case of measuring the current value I in a liquid that contains biopolymers, the current value I includes a component of the base current Ib, which is measured when no biopolymers exist between the nano-electrodes 34, and a component of a sample current Is, which is measured when biopolymers have passed through between the nano-electrodes 34. The sample current Is corresponds to the tunneling current flowing between the biopolymers and the nano-electrodes 34.

As illustrated in FIG. 22, the sample current Is has a larger current value than the base current Ib. Thus, the measured current value I can be separated into the component of the base current Ib and the component of the sample current Is. Since the sample current Is in step S331 is not a value measured when the interelectrode distance is set to a desired distance, the sample current Is cannot be used as experimental data.

In step S331, the controller 90 extracts the component of the base current Ib from the measured current value I and calculates the reference current Ic from the extracted component, the reference current Ic being a current value of the base current Ib in the case where the tunneling current does not flow between the nano-electrodes 34.

Next, the controller 90 calculates a target total current value Ia (step S332). The target total current value Ia is a value of the tunneling current between the nano-electrodes 34, which corresponds to the target distance of the interelectrode distance d. Specifically, first, the target interelectrode distance is substituted into the interelectrode distance d in Expression (4) to calculate the target tunneling current value Iu. The target tunneling current value Iu is a value of the tunneling current that corresponds to the target distance of the interelectrode distance d. Then, the target tunneling current value Iu is added to the reference current Ic to calculate the target total current value Ia.

Thereafter, the controller 90 operates the pushing-up device 93 to perform steps S333 to S335 in order to arrange the nano-electrodes 34 at target positions in which the base current Ib of the measured current value I matches with the target total current value Ia.

First, the controller 90 operates the pushing-up device 93 so as to make the present base current Ib closer to the target total current value Ia and to change the interelectrode distance d (step S333). In the present embodiment, an upper limit value for the amount of change that can be made by one execution of step S333 to the voltage Vp applied to the piezo-actuator 942 is determined. Thus, a maximum amount of change that can be made by one execution of step S333 to the interelectrode distance d is determined.

Next, the controller 90 stands by for a predetermined second standby time t2 (step S334). In this way, the controller 90 waits until the influence of the transient phenomenon caused by the change in the interelectrode distance d in step S333 becomes small enough. As a result, it is possible to reduce the occurrence of errors in the measured current value, resulting from the transient phenomenon during current measurement in the subsequent step S335.

The second standby time t2, which is the standby time in step S334, is calculated based on the time constant $\tau1$ having the smallest value, the time constant $\tau2$ having the second smallest value, and the time constant $\tau3$ having the third smallest value among the five time constants $\tau1$ to $\tau5$ calculated in the feature-quantity analysis processing in step S100. For example, the second standby time t2 may be calculated by multiplying an average value of the time constants $\tau1$, $\tau2$, and $\tau3$ by a predetermined real number.

Thereafter, the controller 90 causes the ammeter 96 to measure the current value I (step S335).

Then, the controller 90 determines whether the base current Ib of the current value I measured in step S335 falls within a predetermined range of current values (step S336). The predetermined range used in the determination in step S336 is set using the target total current value Ia as a reference. For example, whether the base current Ib falls within a range of plus or minus 0.0005 nA from the target total current value Ia may be used as a reference.

When it is determined in step S336 that the base current Ib has not reached a value within the predetermined range (No in step S336), the controller 90 returns to step S333 and continues to adjust the interelectrode distance d.

On the other hand, when it is determined in step S336 that the base current Ib has reached a value within the predetermined range (Yes in step S336), the controller 90 completes the interelectrode-distance adjustment processing in step S300.

Next, a procedure of the interelectrode-distance adjustment step performed in a large gap mode in step S340 will be described with reference to FIG. 21. When the interelectrode distance during the current measurement is relatively large, the value of the tunneling current at this interelectrode distance is relatively small. When the value of the tunneling current is smaller than the noise component of the reference current Ic, it becomes difficult to detect a difference between the reference current Ic and the target total current value Ia. Therefore, even if electrode positions are tried to be set by the same method as that used in the small gap mode, it is difficult to accurately set the electrode positions that provide a desired interelectrode distance. In view of this, the electrode positions are set in the large gap mode described later so as to provide a desired interelectrode distance.

Figure 23:
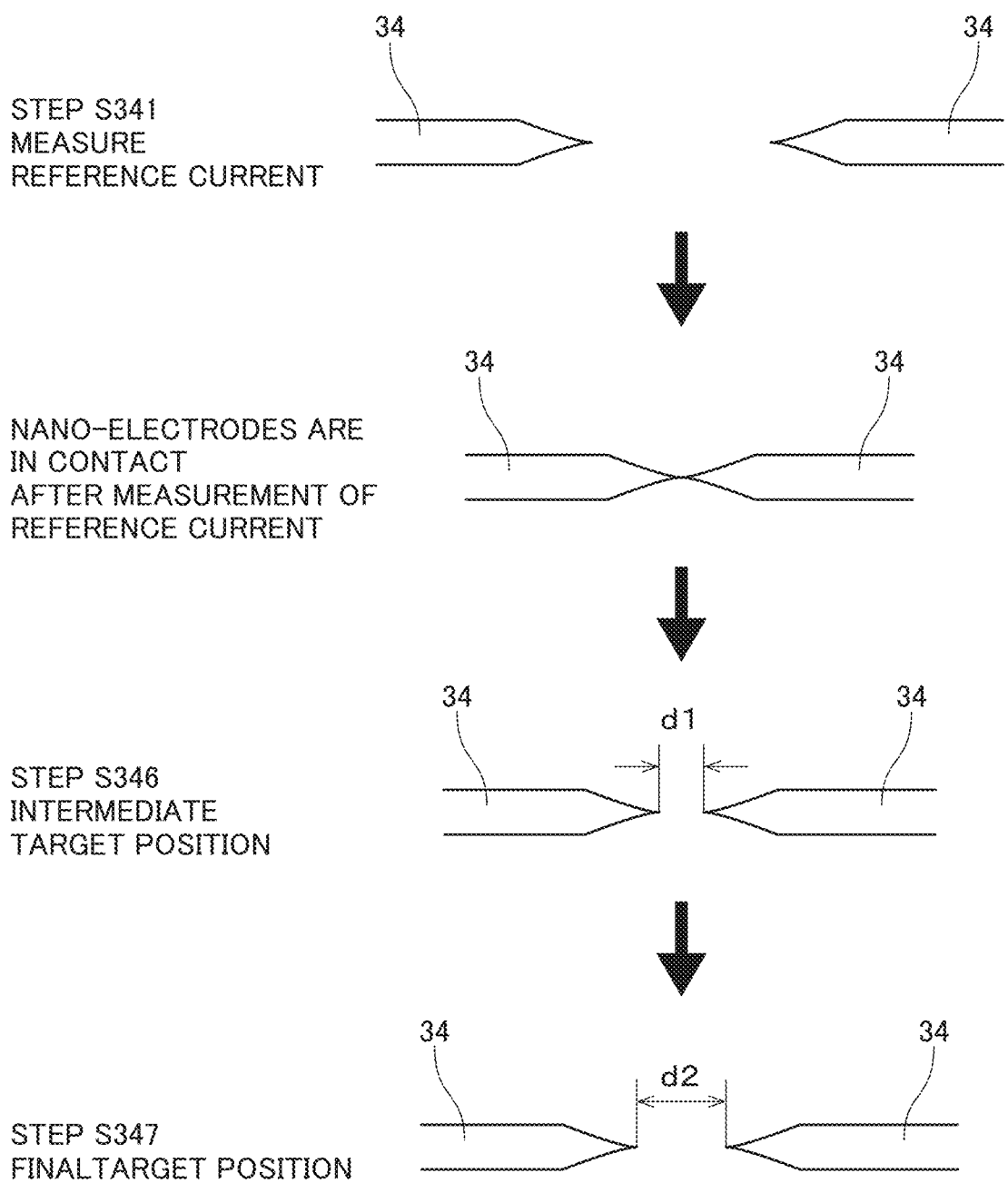
FIG. 23 is a schematic diagram illustrating the space between the nano-electrodes in the interelectrode-distance adjustment step performed in the large gap mode.

FIG. 23 is a schematic diagram illustrating the space between the nano-electrodes 34 in the interelectrode-distance adjustment step in the large gap mode in step S340. As illustrated in FIG. 23, first, the reference current Ic is measured, with the interelectrode distance being set large enough so as not to produce a flow of the tunneling current between the nano-electrodes 34 (step S341). After the measurement of the reference current Ic, the pushing-up device 93 is returned to the position in which the tip portions of the nano-electrodes 34 are in contact with each other. The measurement of the reference current Ic is made in the same manner as in step S331 in the small gap mode.

Next, the controller 90 calculates an intermediate target total current value Id and a manipulated variable of movement $\Delta Vp$ (step S342). Specifically, first, an intermediate tunneling current value Iv is calculated. The intermediate tunneling current value Iv is a tunneling current value corresponding to an intermediate interelectrode distance d1 that indicates an intermediate target position. The intermediate interelectrode distance d1 indicating the intermediate target position is an interelectrode distance smaller than the target interelectrode distance d2 indicating a final target position. The intermediate tunneling current value Iv is calculated by substituting the intermediate interelectrode distance d1 into the interelectrode distance d of Expression (4). Then, the intermediate tunneling current value Iv and the reference current Ic measured in step S341 are added to calculate the intermediate target total current value Id. The intermediate interelectrode distance d1 is set such that the intermediate tunneling current value Iv becomes sufficiently larger than the noise component of the reference current Ic.

Meanwhile, the manipulated variable of movement $\Delta Vp$ is a manipulated variable required for movement from the intermediate interelectrode distance d1 indicating the intermediate target position to the target interelectrode distance d2 indicating the final target position. This manipulated variable of movement $\Delta Vp$ is specifically the amount of change in the voltage Vp applied to the piezo-actuator 942, required to achieve the movement from the intermediate interelectrode distance d1 to the target interelectrode distance d2. The manipulated variable of movement $\Delta Vp$ is obtained based on the estimation function obtained in the calibration processing in steps S101 to S111. That is, the manipulated variable of movement $\Delta Vp$ is obtained from the relationship expressed by Expression (11) below, using Expression (3) and the proportionality factor $\alpha$ obtained for the interelectrode distance d and the applied voltage Vp in the calibration processing.

[Math. 11]

$$d2-d1=\alpha \cdot \Delta Vp \tag{11}$$

Then, the controller 90 operates the pushing-up device 93 to perform steps S343 to S345 in order to arrange the nano-electrodes 34 in intermediate target positions in which the base current Ib of the measured current value I matches with the intermediate target total current value Id. In this way, the interelectrode distance d between the nano-electrodes 34 can be set to the intermediate interelectrode distance d1.

First, the controller 90 operates the pushing-up device 93 so as to make the present base current Ib closer to the intermediate target total current value Id and to change the interelectrode distance d (step S343). Step S343 is performed in the same manner as step S243 in the small gap mode.

Next, the controller 90 stands by for a predetermined second standby time t2 (step S344). In this way, the controller 90 waits until the influence of the transient phenomenon caused by the change in the interelectrode distance d in step S333 becomes small enough. This suppresses the occurrence of errors in the measured current value, resulting from the transient phenomenon, during the current measurement in step S335. For example, the standby time in step S343 may be the same as the second standby time t2 in step S333 in the small gap mode.

Thereafter the controller 90 causes the ammeter 96 to measure the current value I (step S345).

Then, the controller 90 determines whether the base current Ib of the measured current value I in step S345 falls within a predetermined range of current values (step S346). The predetermined range used in the determination in step S336 is set using the intermediate target total current value Id as a reference. For example, whether the base current Ib falls within the range of plus or minus 0.0005 nA from the intermediate target total current value Id may be used as a reference.

When it is determined in step S346 that the base current Ib has not reached a value within the predetermined range (No in step S346), the controller 90 returns to step S343 and continues to adjust the interelectrode distance d.

On the other hand, when it is determined in step S346 that the base current Ib has reached a value within the predetermined range (Yes in step S346), the controller 90 proceeds to step S347. Then, the controller 9 causes the pushing-up device 93 to push the electrode substrate up by an amount corresponding to the manipulated variable of movement $\Delta Vp$ calculated in step S342 (step S347). Specifically, the controller 90 changes the applied voltage Vp to a voltage value obtained by adding the manipulated variable of movement $\Delta Vp$ to the applied voltage Vp corresponding to the intermediate interelectrode distance d1. In this way, the controller 90 sets the interelectrode distance d between the nano-electrodes 34 to the target interelectrode distance d2 indicating the final target position.

Then, the controller 90 stands by for a predetermined third standby time t3 (step S348). In this way, the controller 90 waits until the influence of the transient phenomenon caused by the change in the interelectrode distance d in step S347 becomes small enough. As a result, it is possible to suppress the occurrence of errors in the measured current value, resulting from the transient phenomenon, during subsequent processing for measuring the tunneling current in biopolymers in step S400. After step S349, the controller 90 completes the interelectrode-distance adjustment processing in step S300.

The third standby time t3, which is the standby time in step S348, is calculated based on the time constant $\tau 1$ having the smallest value and the time constant $\tau 2$ having the second smallest value among the five time constants $\tau 1$ to $\tau 5$ calculated in the feature-quantity analysis processing in step S100. For example, the third standby time t3 may be calculated by multiplying an average value of the time constants $\tau 1$ and $\tau 2$ by a predetermined real number.

6. Variations

While one embodiment of the invention has been described thus far, the present invention is not intended to be limited to the embodiment described above.

In the above-described embodiment, the metal layer of the electrode substrate includes only a single pair of connection electrode portions that receive input of electric power from an external source, but the present invention is not limited to this example. One electrode substrate may include a plurality of pairs of electrodes that receive input of electric power from external sources. For example, a voltage for electrophoresis may be applied between the first and second flow paths.

Each element appearing in the above-described embodiment and variations may be appropriately combined within a range that causes no contradictions.

REFERENCE SIGNS LIST

1 Electrode substrate
9 Current measurement apparatus
34 Nano-electrode
50 Flow path
90 Controller
93 Pushing-up device
94 Elevating mechanism
95 Power source
96 Ammeter
942 Piezo-actuator

The invention claimed is:

1. A current measurement method for measuring a tunneling current in a biopolymer passing through between a pair of electrodes, the current measurement method comprising:
   a) arranging said pair of electrodes in a liquid that contains an electrolyte and, while applying a voltage between said pair of electrodes, measuring a current flowing between said pair of electrodes via an electric double layer formed along surfaces of said pair of electrodes;
   b) measuring the current flowing between said pair of electrodes while applying a predetermined voltage, starting from a condition in which no voltage is applied between said pair of electrodes, wherein the said pair of electrodes maintains a fixed interelectrode distance from each other while measuring the current flowing between said pair of electrodes while applying a predetermined voltage; and
   c) calculating a feature quantity resulting from said electric double layer for a value of said current measured in said operation b).

2. The current measurement method according to claim 1, wherein
   said operation b) and said operation c) are performed before said operation a), and
   said operation a) has measurement timing determined based on said feature quantity.

3. The current measurement method according to claim 1, wherein
   said feature quantity is a time constant of said current measured in said operation b).

4. The current measurement method according to claim 3, wherein
   in said operation c), a plurality of said time constants are calculated.

5. The current measurement method according to claim 3, wherein
   said operation b) and said operation c) are performed before said operation a), and
   said operation a) has measurement timing determined based on said time constant.

6. The current measurement method according to claim 4, wherein said operation a) is a calibration-current measurement operation of acquiring a value of said current flowing between said pair of electrodes through an operation of changing an interelectrode distance of said pair of electrodes while applying a predetermined voltage between said pair of electrodes, and said operation a) includes:

p1) waiting for a standby time calculated based on said time constant;

p2) acquiring a value of a voltage to be applied between said pair of electrodes that is used to change said interelectrode distance and the value of said current flowing between said pair of electrodes; and p3) changing said voltage to be applied between said pair of electrodes to change said interelectrode distance.

7. The current measurement method according to claim 6, further comprising:

d) calculating an approximation function by approximating a relationship between a plurality of said voltages to be applied between said pair of electrodes and a plurality of said current values in said operation a).

8. The current measurement method according to claim 6, wherein said standby time in said operation p1) is calculated as a constant multiple of said time constant.

9. The current measurement method according to claim 4, further comprising:

e) measuring a value of a reference current flowing between said pair of electrodes that has an interelectrode distance at which a tunneling current does not flow between said pair of electrodes; and f) calculating a target total current value by adding the value of said reference current measured in said operation e) and a value of a tunneling current corresponding to a target interelectrode distance, wherein said target interelectrode distance indicates a distance between said pair of electrodes at a final target position, said operation e) and said operation f) being performed after said operation b) and said operation c), and being performed before said operation a), and wherein said operation a) includes:

q1) waiting for a standby time calculated based on said time constant;

q2) measuring a base current flowing between said pair of electrodes, wherein said base current is a sum of said reference current and said tunneling current; and q3) manipulating said interelectrode distance between said pair of electrodes to make a value of said base current closer to said target total current value calculated in said operation f), said operation q1), said operation q2), and said operation q3) being repeatedly performed a plurality of times.

10. The current measurement method according to claim 4, further comprising:

g) measuring a value of a reference current flowing between said pair of electrodes that has an interelectrode distance at which a tunneling current does not flow between said pair of electrodes; and h) calculating an intermediate target total current value by adding the value of said reference current measured in said operation g) and a value of a tunneling current corresponding to an intermediate target interelectrode distance, wherein said intermediate target interelectrode distance indicates a distance between said pair of electrodes prior to said pair of electrodes reaching a final target position, said operation g) and said operation h) being performed after said operation b) and said operation c), and being performed before said operation a), wherein said operation a) includes:

r1) waiting for a standby time calculated based on said time constant;

r2) measuring a base current flowing between said pair of electrodes, wherein said base current is a sum of said reference current and said tunneling current; and r3) manipulating said interelectrode distance between said pair of electrodes to make a value of said base current closer to said intermediate target total current value calculated in said operation h), said operation r1), said operation r2), and said operation r3) being repeatedly performed a plurality of times, the current measurement method further comprising:

i) adjusting said interelectrode distance between said pair of electrodes from said intermediate target interelectrode distance to a final target interelectrode distance by manipulating a voltage to be applied between said pair of electrodes to make said interelectrode distance match said final target interelectrode distance, said operation i) being performed after said operation a).

* * * * *